(12) United States Patent
Alroy

(10) Patent No.: US 8,112,260 B2
(45) Date of Patent: Feb. 7, 2012

(54) METHODS FOR IDENTIFYING PROTEIN SPECIFICITY OF BRAIN CELLS THAT EVOKE A GIVEN MENTAL STATE THAT DOES NOT CONTAIN SMALLER CONSTITUENTS

(76) Inventor: Daniel Alroy, New York, NY (US)

( * ) Notice: Subject to any disclaimer, the term of this patent is extended or adjusted under 35 U.S.C. 154(b) by 1239 days.

(21) Appl. No.: 11/778,163

(22) Filed: Jul. 16, 2007

(65) Prior Publication Data

US 2008/0171320 A1    Jul. 17, 2008

Related U.S. Application Data

(63) Continuation-in-part of application No. 09/871,560, filed on May 31, 2001, now Pat. No. 7,680,602.

(60) Provisional application No. 60/208,278, filed on May 31, 2000.

(51) Int. Cl.
G06G 7/58    (2006.01)

(52) U.S. Cl. .......................................... 703/11

(58) Field of Classification Search .................. 703/11
See application file for complete search history.

(56) References Cited

PUBLICATIONS

Bendor D and Wang X. Cortical representation of pitch in monkeys and humans. *Nature*. Aug. 2005. 436(7054):1161-5.
Blanke O et al. Direction-specific motion blindness induced by focal stimulation of human extrastriate cortex. *European Journal of Neuroscience*. 2002. 15: 2043-8.
Brugger B et al. Beyond re-membering: Phantom sensations of congenitally absent limbs. *Proc. Nat. Ass. Sc. USA*. May 2000. 97 (11): 6167-72.
Bruno RM et al. Thalamocortical angular tuning domains within individual barrels of rat somatosensory cortex. *Journal of Neuroscience*. Oct. 2003. 23 (29) 9565-9574.
Chen LM et al. Optical imaging of SI topography in anesthetized and awake squirrel monkeys. *Journal of Neuroscience*. 25 (33) 7648-7659.
Clark TA et al. Discovery of tissue-specific exons using comprehensive human exon microarrays *Genome Biology*. Apr. 2007. 8:R64: 1-16.
Contrera D and Llinas R. Voltage-sensitive dye imaging of neocortical spatiotemporal dynamics to afferent activation frequency. Dec. 2001. *J of Neuroscience*. 21(23): 9403-9413.
De Araujo Iet et al. Representation of umami taste in the human brain. *Journal of Neurophysiology*. Jul. 2003. 90: 313-319.
Herzenberg Ia et al. The history and future of fluorescence activated cell sorter and flow cytometry: a view from Stanford. *Clinical Chemistry*. 2002. 48:10 1819-1827.
Jacobs J et al. Brain oscillations control timing of single-neuron activity in humans. Apr. 2007. *Journal of Neuroscience*.
Pecina S and Berridge KC. Hedonic hot spots in the brain. *Journal of Neuroscience*. Dec. 2005. 25 (50) 11777-11786.
Roe AW et al. Cortical processing of a brightness illusion. *Proc. Nat. Assoc. Sci. USA*. Mar. 2005. 102 (10): 3869-74.
Rolls ET et al. Gustatory responses of single neurons in the caudolateral orbitofrontal cortex of the macaque monkey. *Journal of Neurophysiology*. Oct. 1990. 64:1055-66.
Simon A et al. Gap-junctional coupling between neurogliaform cells and various interneuron types in the neocortex. *Journal of Neuroscience*. Jul. 2005. 25 (27): 6378-6285.
Swatton JE et al. Protein profiling of human postmortem brain using 2-dimensional fluorescence difference gel electrophoresis (2-D DIGE). *Molecular Psychiatry*. 2004. 9: 128-143.
Tiscornia G et al. Design and cloning of lentiviral vectors expressing small interfering RNAs. *Nature Protocols*. 2006. 1: 234-40.
Zheng L et al. Study of gene function based on spatial co-expression in a high-resolution mouse brain atlas. *BMC System Biology*. Apr. 2007. 1: 19. pp. 1-14.
Zhihua Z et al. Odor maps in the olfactory cortex. *Proc. Nat. Acad. Sci. USA*. May 2005. 102 (21): 7724-7729.

*Primary Examiner* — Jerry Lin

(57) ABSTRACT

The invention provides methods for identifying brain cells that determine and can evoke subjective states that do not contain smaller constituents, by establishing a correspondence between intrinsic function of a cell type with its hierarchy of constitutively-expressed proteins. The hierarchy level of a dysfunctional protein is of diagnostic value and is an effective target for therapeutic modification.

1 Claim, 8 Drawing Sheets

METHODS FOR IDENTIFYING PROTEIN SPECIFICITY OF BRAIN CELLS THAT EVOKE A GIVEN MENTAL STATE THAT DOES NOT CONTAIN SMALLER CONSTITUENTS

CROSS-REFERENCES TO RELATED APPLICATIONS

The instant application is a continuation-in-part of the U.S. patent application Ser. No. 09/871,560 filed on May 31, 2001, now U.S. Pat. No. 7,680,602 which claims priority of a Provisional Patent Application Ser. No. 60/208,278 that was filed on May 31, 2000. The non-provisional application is incorporated by reference into the present application.

BACKGROUND OF THE INVENTION

The invention provides means for identifying correspondence between intrinsic function of cell types that determine unitary subjective states with their hierarchy of constitutively-expressed proteins. Identification of the hierarchy level of a dysfunctional protein is of diagnostic value and is an effective target for therapeutic modification.

DESCRIPTION OF THE PRIOR ART

[1.] Symptom suppression drugs. Like Alzheimer disease, Parkinson disease, and cancer, many diseases are age-related. Most current psychotropic drugs suppress the symptoms of these ailments but do not cure them. Additionally, the ratio of the working persons per retiree in the United States has plummeted from 41:1 in 1930 to 3:1 currently, and is projected to fall to 2:1 by 2020. Hence, there is a public health necessity to shift focus to curing disease. The concepts and techniques of molecular biology can provide the means for cure or prevention of chronic diseases. The problem is, while new techniques are typically adopted without delay, the adoption of a new conceptual framework often takes decades. The delay in the application of the concepts implicit in molecular biology to neural function is a primary reason for the absence of methods to cure or prevent neural dysfunction. Addressed below are two conceptual delay factors. One relates to the delayed transformation of neuroscience by molecular biology and the other relates to fifty years delay in recognizing that sensations are evoked in the brain rather than received from the sensory receptors in the peripheral nervous system.

[2.] Molecular biology and neuroscience. Neural function has been viewed, historically, in terms of intercellular connectivity and interaction. Molecular biology has demonstrated that the intracellular molecular constitution of the cell determines it phenotype and intrinsic function. In some respects these two views of neural function are complementary, in others they are not. The current emphasis on neurotransmitters and their receptor and receptor subtypes reflect the delayed recognition that the response of the cell to the binding of a ligand is cell-type-specific.

[3.] The Relation of Mind and Brain.

[3.1] The notion that sensations originates outside the brain. Present-day theories of science (as well current patent classification systems) are based on the assumption that sensations are received from the senses. Some fifty years ago, evidence became available that instead sensations are evoked in the brain. The fact that sensations are not received from the senses is jarring. As a consequence, the acceptance of this fact by leading neuroscientists was delayed to the beginning of the current decade. The fundamental nature of the transition can be appreciated once it is recognized that present-day theories of knowledge are based on the assumption, now known to be false, that sensations are received from sensory receptors. It may take another half century until the implications of the new state of affairs are made explicit.

[3.2] Some basic distinctions. In regards to neuroscience, the following three crucial distinctions have not yet been reflected in extant scientific literature: 1) the distinction between sensations that are innate and those that are not; 2) the distinction between sensory attributes that are the result of distributed neural function and localized neural function and 3) the distinction between precepts that contain smaller constituents and those that do not.

[3.3] The causal locus of neural function. The molecular constitution of the cell determines its function. This tenet is implicit in molecular biology; explicit in structural biology, but denied in the computer metaphor of brain function. Specifically, the computer metaphor postulates that neural function and neuroanatomy are dissociable. The influence of the computer metaphor on neuroscience has delayed recognition that the molecular constitution of brain cells determines their function. More generally, this metaphor handicaps recognition that elementary cellular function is highly localized. The displacement of the causal locus of cellular function from intracellular to intercellular, shifts focus from causes to symptoms.

[4.] Pain. The conceptual, rather than the technical, nature of the obstacles to the development of effective medication are illustrated by conflicted views about the nature of pain. During the heyday of Behaviorism, pain was defined as pain behavior. On that basis, children were operated upon without anesthetics—they were just paralyzed with curare. Later, pain was assumed to be a physical activation of the afferent C-fibers. On that basis, numerous needless amputations were made in a vain attempt to alleviate chronic pain in the extremities. The computer metaphor proposed that pain is algorithmic and not neuroanatomic. Currently, pain is assumed to be an emergent property of distributed networks in the brain. Drug development targets pathway-related neurotransmitters and their receptors. The binding of the same type of ligand to the same receptor subtypes elicits diverse cell-type-specific response (e.g. the cell-type-specific response of target neurons of dopamine binding to D2 receptors in each of the four main pathways). The development of effective medication for alleviating chronic pain remains an unmet challenge.

OBJECTS AND ADVANTAGES

[1.] From symptom suppression to cure. The invention provides cell-type-specific molecular basis for the diagnosis and treatment of neural function that underlies psychological dysfunction. In contrast to drugs that target neurotransmitters and their receptors, cell-type-specific and locus-specific therapy is a basis for prevention and cure.

[2.] Some Basic Elements of the Invention.

[2.1] A basic tenet. It is generally agreed that neural function determines mental states. A basic tenet of the invention is that the molecular constitution of the cell determines its function. Thus, the molecular constitutions of brain cells that determine neural function also determine mental states.

[2.2] Unitary subjective states. Percepts that contain smaller constituents ultimately consist of unitary subjective states—those that do not contain smaller constituents. The focus of the invention is on brain cells that determine the qualitative aspects of these unitary subjective states.

[2.3] Hierarchical organization. Modalities, submodalities and submodality elements of exteroreceptor-based sensations form a three-level hierarchy. In primates, this hierarchy is spatially represented in each hemisphere of the cerebral cortex. Brain cells that determine the subjective quality of any submodality element of sensation are located within the corresponding submodality-specific area, which in turn is located within the corresponding modality-specific cortical area. This hierarchical organization and its spatial representation in the brain exist for all mental states, including interoreception, emotion and cognition.

[2.4] The molecular constitution of the cell. The molecular constitution of the cell is here characterized by its constitutively-expressed proteins, hereafter called protein specificity. The primate body contains about 220 different cell types in terms of phenotype (attributes such as size and shape). For example, one of these cell types, the olfactory receptor cell, has about 370 cell subtypes in humans. Thus, the number of cell types by protein specificity is much larger than by phenotype. Moreover, unlike phenotype, protein specificity determines the intrinsic function of cell types.

[3.] Similarity and contrast with cytoarchitecture. The invention may be viewed as a molecular version of cytoarchitecture. The cytoarchitecture of Brodmann areas, for example, identifies some functional areas in the cerebral cortex on the basis of the laminar distribution of cell types. These functional areas are identified without reference to interactivity or connectivity. The invention, likewise, identifies locus-specific function without reference to interactivity or connectivity. Unlike the cytoarchitecture of Brodmann areas, the invention applies generally and is not limited to the cerebral cortex. The crucial difference, however, is that the invention characterizes a cell type by its subcellular protein specificity. As a consequence, the invention identifies intrinsic function with single cell resolution. Such protein specificities also determine the intrinsic function of brain cells that determine and can evoke mental states.

[4.] Hierarchy of cell-type-specific proteins. The constitutively-expressed proteins of any cell type form a hierarchy which can be represented by a tree. Proteins found in all cell types form the tree-trunk. Branch-tip proteins of any cell types are unique relative to branch-tip proteins of other cell types that have the same proximate branch-node proteins. The inactivation of any of these branch-tip proteins eliminates the function of its cell type without eliminating the function of cell types represented by the other branch-tip proteins sharing the proximate branch-node proteins. The hierarchy level of proteins determines the scope of their function and dysfunction. The branching pattern from the tree-trunk to any branch-tip is unique. Collectively, the branch-tips represent the number of cell types in the organism.

[5] Neural correlates of consciousness. The invention proves causal connection between brain cells and a subjective state. It is the first to do so. Proof of this is made possible by the conjunction of several factors that include: 1) the recognition that sensations are evoked in the brain and not received from the senses, 2) the recognition that unitary subjective states are evoked by locus-specific brain cells and are not an emergent property of distributed networks, and 3) the identification of the intrinsic function of brain cells by their protein specificity.

[6.] Molecular psychophysics. The conceptual framework of the invention introduces the correlation of unitary subjective states with the protein specificity of locus-specific brain cells. The systematic application of this conceptual framework may be called molecular psychophysics.

[7.] A threefold transformation. The identification of the causal locus of neural function to be intracellular involves a threefold shift in the causal locus relative to prior art:
[7.1] from the PNS to the CNS
[7.2] from pathways to loci and
[7.3] from the intercellular to the intracellular

[8.] Utility. The invention takes the cell to be the basic unit of neural function and dysfunction. Any mature, differentiated cell type is characterized by its hierarchy of constitutively-expressed protein classes. The hierarchy level of a protein determines the scope of the effects of its inactivation. Identifying the hierarchical level of a dysfunctional cell-type-specific protein forms a novel basis for diagnosing and treating the neural basis of psychological dysfunction.

SUMMARY

[1.] Overview.

[1.1] NCC and utility. The invention identifies neural correlates of consciousness (NCC). It does so by first conceptually identifying the hierarchy of constitutively-expressed proteins of brain cells that determine and can evoke subjective states that do not contain smaller constituents. The invention then actually identifies some of these cells and proteins from extant data. Thus, hierarchy-specific variance from normal protein specificity of any given cell type can become a basis for diagnosis and is an effective target for therapeutic modification.

[1.2] Unitary subjective states. All experience is the result of brain function and is thus subjective. Exteroreception, interoreception, emotions and cognitions are some categories of subjective states. Vision, hearing, touch taste and smell are five of the sensory modalities of exteroreception. Sensory modalities, submodalities and submodality elements form a three-level hierarchy. Sensory modalities contain submodalities. Color and visual motion-direction, for example, are submodalities of vision. Red, green, yellow and blue are submodality elements of color. Similarly, up, down, right, left and the four diagonals are submodality elements of visual motion-direction. Submodality elements of sensation are not further divisible—they do not contain any smaller constituents. Submodality elements of exteroreception exemplify a more general class of unitary subjective states. Thirst, for example, is a unitary subjective state of interoreception while fear is a unitary subjective state of basic emotions. The description below uses examples primarily from exteroreception but the methods presented apply to all unitary subjective states.

[1.3] Representation of submodality elements of sensation in the cerebral cortex. The three-level hierarchy of sensory modalities, submodalities and submodality elements is spatially represented in the cerebral cortex. Each cerebral hemisphere has a self-contained area for each sensory modality. Brain cells representing any submodality element are located within their corresponding submodality-specific area. Any submodality-specific area receives feed-forward input from within its modality-specific area. This feed-forward input defines submodality-specific areas as located in secondary, or non-primary, modality-specific areas. In the somatosensory cortex SI, for example, areas 1 and 2 receive feed-forward input from areas 3a, 3b or both. Areas 1 and 2 are, therefore, non-primary areas of the somatosensory cortex.

[1.4] Localization. In mammals each side of the body is represented in the contralateral hemisphere of the somatosensory cortex. In rodents, for example, each whisker is represented by a column in the contralateral somatosensory cortex.

Other sensory modalities and submodalities are represented in one region of each hemisphere.

[1.5] Cells that determine and can evoke a given submodality element of sensation. The stimulation of brain cells that determine a particular submodality element of sensation evoke that sensation in a conscious person who attends to the stimulus. Here are three aspects of such an event: 1) the person will experience that submodality element of sensation, 2) if so instructed, the person will exhibit a behavioral response signifying the presence of that sensation and 3) the stimulated cells that evoke the sensation will manifest increased activation. The inactivation of these cells selectively eliminates the above three manifestations without eliminating responses to stimuli characteristic of other elements within the same submodality.

[1.6] Protein specificity. The phenotype and the intrinsic function of the cell are manifestations of its molecular constitution. The molecular constitution of any cell type in an organism is characterized by its constitutively-expressed proteins. Those proteins form a hierarchy, which reflects the cell's organ, tissue and tissue-specific cell type membership. Proteins of a hierarchy-level function form a class that functions conjunctively: the dysfunction of any protein eliminates the function of the entire class. Consequently, the function of all cell types containing this protein class is eliminated. The protein specificity of cells that determine and can evoke a given submodality element of sensation reflects that cell's membership in the hierarchy of its modality, submodality and submodality element.

[1.7] Cell types subtypes and sub-subtypes. The hierarchy of proteins that characterize a cell type can be illustrated, for example, in reference to photoreceptors in humans. Cones and rods are two cell subtypes of photoreceptors. Cones have three photoreceptor sub-subtypes: the short, medium and long wavelength photoreceptors. Thus, photoreceptors, cones and long wavelength cones represent a three-level hierarchy where 1) proteins that determine the most specific level (wavelength-specific cones) are unique relative to each other, 2) all cones have in common cone-specific proteins and 3) cones and rods have in common photoreceptor-specific proteins. Mutated long wavelength cone photoreceptors cause red-blindness, but leaves unaffected the function of short- and medium-wavelength specific cones. Dysfunction of proteins that are cone-specific causes complete colorblindness (peripheral achromatopsia), but leave unaffected the function of rod photoreceptor cells. Mutation in a photoreceptor-specific protein causes dysfunction in general vision (e.g. Retinitis Pigmentosa). Inactivating a protein is hierarchy-level dependent. Proteins that characterize cells that have a proximate protein class in common are unique relative to each other.

[2.] Major identification stages. Listed below are the main stages of identifying the locus and protein specificities of the cells of interest. The identification stages are illustrated in reference to the sensation of sweet taste. The five known submodality elements of basic tastes are sweet, salty, sour, umami and bitter. These submodality elements are present in rodents and primates. Cells that determine and can evoke any of the basic taste sensations are located in the secondary gustatory cortex. Cells of interest are often identified in rodents first, then in non-human primates and finally in humans.

[2.1] Psychophysics. Techniques of psychophysics are used to establish a one-to-one correspondence between each basic taste and the tastant (external stimulus) that elicits it, and subsequently establish a one-to-one correspondence between each basic taste and a behavioral response, such as pressing a particular button or lever. As a result, a one-to-one correspondence is established between each tastant and a behavioral response. The manifestation of such a response following the correct stimulus signifies the presence of a given taste sensation, while the absence of that response signifies the absence of the correlated sensation.

[2.2] Locus identification. Cells that determine and can evoke a particular submodality element of sensation are located in the corresponding submodality-specific cortical area of each cerebral hemisphere. Stimuli, and especially repetitive stimuli, that are specific to a given submodality element of sensation, induce the transient expression of transcription factors known as immediate early genes (IEGs). In response to such stimuli, columnar cells in layers 2 and 3 in the corresponding submodality-specific cortical areas express the immediate early gene c-Fos. Antibodies raised against a particular IEG make it possible to identify the IEG expressing cells.

[2.3] Cell sorting. After about seven days of having mice receive stimulus specific to a given submodality element of sensation, such as the ingestion of sweet-tasting liquids, the brain tissue containing the cells identified by c-Fos antibodies is removed, sectioned, stained with fluorescence and prepared as a single cell suspension, then sorted from other cells using flow cytometry.

[2.4] Cell-type-specific protein identification. These c-Fos expressing cells also contain cell-type-specific mRNA and proteins. The expressed cell-type-specific mRNA is identified by using either microarrays, such as AFFYMETRIX© GeneChip™ whole transcript (WT) array, or the expressed proteins can be identified directly by using two-dimensional fluorescence difference gel electrophoresis (2-D DIGE). These identifications are made by contrasting cells of mice that were subjected to one type of stimuli (e.g. ingestion of sweet-tasting liquids) with controls (e.g. those that ingested umami-tasting liquid with monosodium glutamate).

[2.4] Validation of locus identification by selective inactivation. A protein can be inactivated by gene silencing, disruption of mRNA translation or use of antibodies, if the protein is cell-surface membrane-bound. RNA interference (RNAi) is one method of disrupting mRNA translation. An antisense sequence is constructed and amplified. Then brain cells are transfected with that mRNAi sequence by using replication-deficient lentiviral vectors. The inactivation of cell-type-specific proteins in cells that determine and can evoke the sensation of sweet taste selectively eliminates 1) the perceived sensation in response to tasting sugar, 2) the correlated behavioral response and 3) the transient increased cellular activation. This inactivation of cell-type-protein eliminates the function of the corresponding cell type, leaving unaffected the function of the related cell types. The elimination of the cell types that determine and can evoke the sensation of sweet taste leaves unaffected the response of mice to any of the other four tastants. Selective inactivation proves a causal connection. Thus, if the inactivation of certain cells in the secondary gustatory cortex selectively eliminates the behavioral response to tasting sugar proves that those cells are ones that evoke the sensation of sweet taste. More generally, the above method identifies cellular and molecular correlates of unitary subjective states.

[2.5] Identifying human homologs of murine proteins. The human homologs of murine mRNA/cDNA are identified from DNA databases.

[2.6] Haplotype-based testing in humans. Proteins that are identified first in the mouse or the rat are then subjected to validation tests in non-human primates. In humans, inactivation test is replaced by reversible down-regulation. Human subjects should be selected to be homogenous with regard to Y chromosome and mitochondrial DNA haplotype markers. The first group to be so tested should be the earliest (Y chromosome marker M91 and mitochondrial marker L1).

[3.] Alternative identification methods. The invention can identify the cells and proteins of interest from extant data and protein databases. If not found, the proteins of interest are identified first in the mouse or the rat and then their human homologs are retrieved from DNA databases. Human brain tissue samples are used when they contain the cells of interest.

[3.1] Extant data. Section H below provides several examples, which demonstrate how the application of the invention to extant data available in DNA and protein databases and in printed form yields actual identification of cells that determine unitary subjective states. Such identifications can also be made by searching DNA and protein databases.

[3.2] Use of non-human animals. The cell-type-specific proteins are identified in mouse or the rat first and then their human homologs are retrieved from DNA databases.

[3.3] Use of human brain tissue samples. When cell data about locus and protein specificities that determine a given unitary subjective states is not found in extant information, the next alternative technique is using DNA and protein microarrays on human brain tissue samples.

[4.] Recapitulation and Utility.

[4.1] Three basic notions: The identification of cell types that determine unitary subjective states, such as the gustatory cortex cells that determine and can evoke the sensation of sweetness, is the result of the conjunction of three basic notions:

Sensations are evoked in the brain. They are not received from the senses.
Unitary subjective states are determined and can be evoked by locus-specific brain cells.
Protein specificity determines intrinsic function of cells and thus unitary subjective states.

[4.2] NCC. The conjunction of these three basic notions makes selective inactivation applicable to the relations between cells and unitary subjective states. Selective inactivation proves a causal connection. Thus, the invention identifies neural correlates of consciousness on the cellular and molecular levels. It is the first to do so.

[4.3] Updating the cell-centered database. Cells that determine and can evoke a given unitary subjective state are a subset of brain cells, which are a subset of the cells in the body. Mapping the hierarchy of constitutively-expressed proteins in a haplotype-specific manner forms a new type of cell-centered database.

[4.4] Utility. The haplotype-specific hierarchy of a constitutively-expressed, cell-type-specific proteins, forms a basis relative to which cellular dysfunction can be diagnosed. The hierarchy level of a dysfunctional protein is then an effective target for therapeutic intervention.

BRIEF DESCRIPTION OF THE DRAWING FIGURES

DETAILED DESCRIPTION

Part I: The Conceptual Framework
A. Unitary Subjective States

Figure 1:
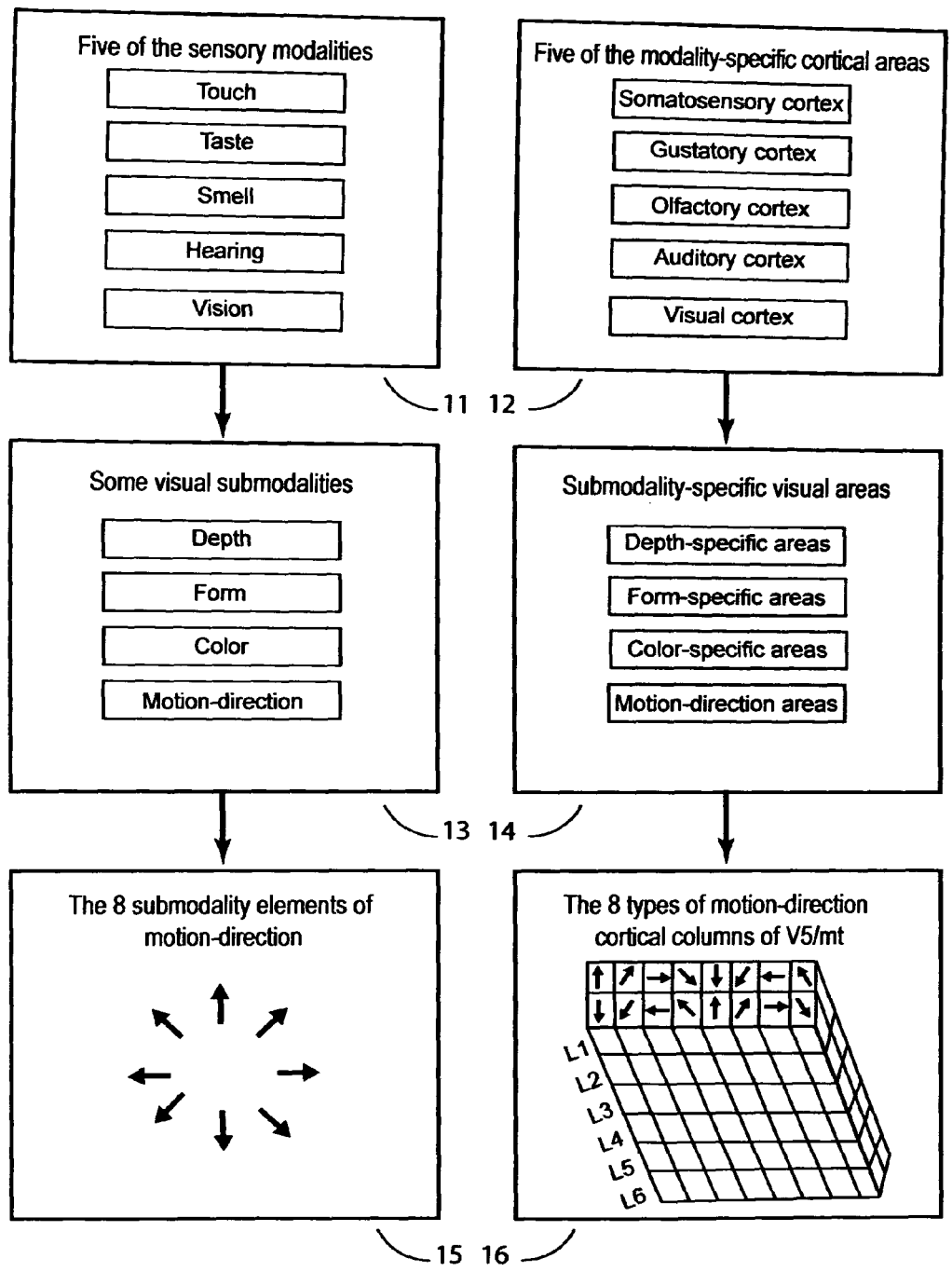
FIG. 1 is an illustrative view of the three-level hierarchy of sensory modalities, submodalities, and submodality elements, and their spatially self-contained representation in each hemisphere of the cerebral cortex.

[1.] Submodality elements of exteroreceptor-based sensations (FIG. 1). Information about the outside world is provided by exteroreceptor-based sensory modalities that include vision, hearing, touch, taste and smell, 11. Sensory modalities contain submodalities. Some of the submodalities of vision, for example, include depth, form color, and motion-direction, 12. Submodalities contain submodality elements. Visual motion-direction, for example, contains eight submodality elements: upward motion, downward motion, motion to the right, motion to the left, and motions in the four diagonal directions, 15. Unlike modalities and submodalities, submodality elements do not contain smaller constituents: they are indivisible or unitary subjective states. Unitary subjective states include the opponency relationship. Opponency is a basic biological mechanism. Any two opponent unitary subjective states (e.g. black/white, up/down, hunger/satiety, hot/cold, pain/pleasure) are typically interconnected. The invention applies to all unitary subjective states, including interoreceptor-based sensations, basic emotions and elementary cognitions. The invention is initially explained in reference to submodality elements of exteroreception-based sensation and column-specific cells located in submodality-specific cortical areas that that determine and can evoke any such submodality element of sensation. However, the principles described herein below may apply to locus-specific neural clusters that determine and can evoke any unitary subjective state.

[2.] Innateness. Unitary subjective states are innate: they are present at birth prior to any postnatal experience. Pupils are dilated by liking and constricted by disliking. The newborn likes sweet and dislikes bitter. The startle response is another example of innate and universal behavior. Similarly, the five known basic tastes—sweet, salty, umami, sour and bitter—are innate. The sensations of sweet and bitter are not received from taste receptors in the tongue; instead their subjective quality is determined by locus-specific neurons in the secondary neurons in the secondary gustatory cortex. Similarly, stimulating the auditory cortex of children born deaf elicits sensations of sound. This is the basis of the ability of congenitally deaf children to hear in response to electric stimulation of the auditory nerve by auditory prostheses. The auditory cortex is stimulated via the cochlea by cochlear implants or via the auditory brain stem in cases where the auditory nerve is dysfunctional. Auditory prostheses can also stimulate the auditory cortex directly. The use of auditory prostheses proves that sound is not a property of air vibration, and that the sensation of sound does not originate in the ears. Some persons that are born without a limb experience sensations of a limb they never had. The prior notion was that sensations are received from the senses and then are "re-presented" in the brain. This assumption excludes even the possibility of identifying brain cells that determine and can evoke said sensations in the absence of input from sense receptors. Thus, the jarring fact that submodality elements of sensations are innate and evoked in the brain is of fundamental importance. Understanding the nature of pain, for example, is transformed by the recognition that it originates in the brain.

[3.] Some Other Categories of Unitary Subjective States.

[3.1] Interoreception and homeostasis. Hunger and thirst are examples of interoreception. Hunger is the part of the energy homeostasis system, which involves voluntary action. Hunger for glucose, hunger for carbohydrates, hunger for fats and hunger for proteins, appear to be four unitary sensations. Within set-points, homeostasis of the internal environment is maintained by non-conscious autonomic mechanisms. When these mechanisms are insufficient, the hypothalamus evokes an interoreceptor-based sensation with a negative affect. This sensation prompts a voluntary action. Restoration of homeostasis then evokes a transient positive affect and a return to non-conscious automatic regulation. Like any sensation, the sensations of hunger are determined by the protein specificity of locus-specific cells.

[3.2] Affective states. Sensations have a spatial attribute (a body location or external space), but they lack a temporal dimension: they occur in the present. The opposite applies to emotions. Emotions are devoid of spatial dimension, but they do have the temporal dimension. Fear, for example has a future dimension, while regret concerns the past. These twin attributes make emotion a central-state agency of the individual. Affective states are extrinsically associated with sensations and thus are dissociable. The newborn, for example, likes sweetness. Sweet taste is determined in the secondary gustatory cortex, while the positive affect of sweet taste is determined by cell-type-proteins in the nucleus accumbens.

[3.3] Cognition Percepts combine sensation and cognition. Sensations are modality-specific, while cognition is basically amodal. A percept, such as an image on a computer screen is pattern-rich. In contrast, submodality-elements of sensation are pattern-poor or pattern-free. The spatial and temporal pattern of picture elements is contributed by amodal cognitive mechanisms. Cognition provides the spatial and temporal framework within which perception occurs. Brodmann area 39 is involved in some basic cognitive functions including pattern generation and recognition. The brain's pattern generation and recognition faculties underlie the aesthetic sense, which associates successful identification of complex patterns with positive affect (e.g. attractiveness).

B. Psychophysics

[1.] Correlating Submodality Elements of Sensation with Behavioral Responses

[1.1] A procedure to indirectly observe subjective states. Using techniques of psychophysics, a one-to-one correspondence is established, first between elements of a given submodality and the external stimuli that elicit each, then between those submodality elements and behavioral responses, so that a one-to-one correspondence is established between stimuli and behavioral responses. As a result, a response following the correlated stimulus signifies the presence of the corresponding element of sensation, while the absence of such response signifies the absence of that element of sensation. From that point on, the publicly observable responses to stimuli represent subjective states which are not publicly observable.

[1.2.] Correlating submodality elements of sensation with voluntary behavioral responses. The sensation of sound is determined and can be evoked by cells located in the secondary auditory cortex. The sensation of auditory pitch does not contain any smaller constituents and is thus a unitary subjective state. Let Q designate any unitary subjective state and let S designate a Q-specific external stimulus. If Q is the middle C pitch then stimulus S is air vibration frequency of 261.63 Hz; if Q is the middle A pitch, then the stimulus S is air vibration frequency of 440 Hz. When the frequency of air vibration is increased gradually, the sensation of pitch makes step-like transitions. If Q is any such subjective transition, then pressing a key is the Q-specific voluntary response R. Assume that a computer records said key depressions with the associated vibration frequencies. A person with normal hearing would press the key about 3,000 times in response to the gradual increase in air vibration frequency from 20 Hz to 20,000 Hz. Testing a representative number of persons with normal hearing can generate a standard against which the test of an individual can serve diagnostic purposes.

[2.] Correlating submodality of sensations with non-voluntary responses. Characteristic appetitive or aversive responses to stimuli provide a basis for establishing correlations between stimuli and responses which do not depend on voluntary behavioral responses. Non-invasive brain imaging can identify brain loci with a resolution approaching that of a single cortical column. The use of such non-invasive imaging methods make it possible to identify loci manifesting increased or decreased activation in response to stimuli.

C. Cortical Loci of Cells that Determine a Given Submodality Element of Sensation

[1.] Cortical representation of submodality elements (FIG. 1). In primates, the three-level hierarchy of exteroreceptor-based sensory modalities, submodalities and submodality elements is spatially represented in the cerebral cortex. Each of the five sensory modalities, for example, is represented by a self-contained area in each hemisphere, 12. Each cortical modality-specific area contains submodalities. Thus, for example, the visual submodalities of depth perception, form perception, color vision, and visual motion-direction, for example, are located in the visual cortex, 14. Finally, cells representing submodality elements are located within their corresponding submodality-specific cortical areas. Cortical columns representing each of the eight motion-direction submodalities are located in the motion-direction submodality area 5 in the medial temporal cortex (V5/MT) of the visual cortex, 16.

[2.] Regions, areas and loci. It is useful to have a terminological convention that reflects spatial extent of the representation of sensory modalities, submodalities and submodality elements. Let the term region designate the spatial representation of a sensory modality; let the term area designate the spatial representation of a submodality. Finally, let the term locus designate the spatial extent of a neural cluster such as the cortical column or minicolumn.

[3.] Stimuli that may lead to conscious awareness are mediated through the thalamus. Voluntary responses to stimuli involve conscious states while automatic responses typically do not. Stimuli that may lead to voluntary responses are mediated through the thalamus, while those that lead to automatic response typically bypass the thalamus. Thus, information from olfactory receptor cells that projects to the olfactory bulb and is not routed through the thalamus leads to non-conscious automatic response (e.g. pheromones). In contrast, information from the olfactory bulb that is routed through the thalamus to the olfactory cortex can give rise to sensation of odor.

[4.] The distinction between primary and secondary modality-specific cortical areas. Primary modality-specific cortical areas are the initial targets of projections from modality-specific thalamic nuclei. Secondary modality-specific cortical areas are those that, in addition, receive feedforward projection from within these modality-specific areas. For this reason, in the sensory cortex, neural clusters that determine the quality of unitary subjective states are located in secondary modality-specific areas. Consider, for example, the somatosensory cortex SI. It consists of areas 3a, 3b, 1 and 2. Areas 3a and 3b are the initial targets for the thalamocortical afferents. Areas 1 and 2 receive feedforward input from 3a or 3b or both. In this sense, areas 1 and 2 are secondary. Area 1 is submodality-specific for light touch while area 2 is intramodal integration area.

[5.] Laterization. Most unitary subjective states are represented in each cerebral hemisphere. The right and left sides of the body are represented in the contralateral hemispheres. Handedness and language are other examples of laterization. Laterization is one factor that is considered in identifying the locus of cells that determine any given unitary subjective state.

[6.] Cortical Columns, Minicolumns and Single Cell Responses.

[6.1] Cortical columns. The visual submodality of motion-direction contains eight elements: up, down, right, left and the four diagonal directions. Each of these eight submodality elements is represented by one type of cortical column that is located in area V5/MT of the visual cortex, which is submodality-specific for motion-direction. Each of the eight types of columns determines the qualitative aspect of one of the eight motion directions. A conscious person who attends to the stimulus would experience the visual sensation of one of eight motion directions upon the stimulation of the corresponding motion-direction columns in visual area V5/MT.

[6.2] Cortical minicolumns. In rodents, each whisker is represented by a cortical column in the contralateral hemisphere of the somatosensory cortex. Each of these columns contains tactile motion direction minicolumns. Each type of motion-direction minicolumn determines and can evoke the unitary subjective state of a tactile motion-direction in a particular direction.

[6.3] Single cell responses. Intrinsic cell-type-specific function is complex. That complexity it suggested by single cell recordings and demonstrated when the in vitro function is similar to the in vivo function. Clock neurons of the hypothalamus and place cells of the hippocampus are examples.

[7.] Evoking sensation by external, direct or endogenous stimulation of neural clusters. Upon stimulation, cells that determine a particular submodality element of sensation evoke that sensation in a conscious person who attends to the stimulus. These cells can be stimulated in one of three ways: 1) through ordinary stimulation of sensory receptors in the PNS, 2) by their external direct stimulation (e.g. electrically) or 3) by endogenous stimuli. These stimuli modes are discussed in reference to the sensation of light touch and the sensation of sweet taste.

Figure 2:
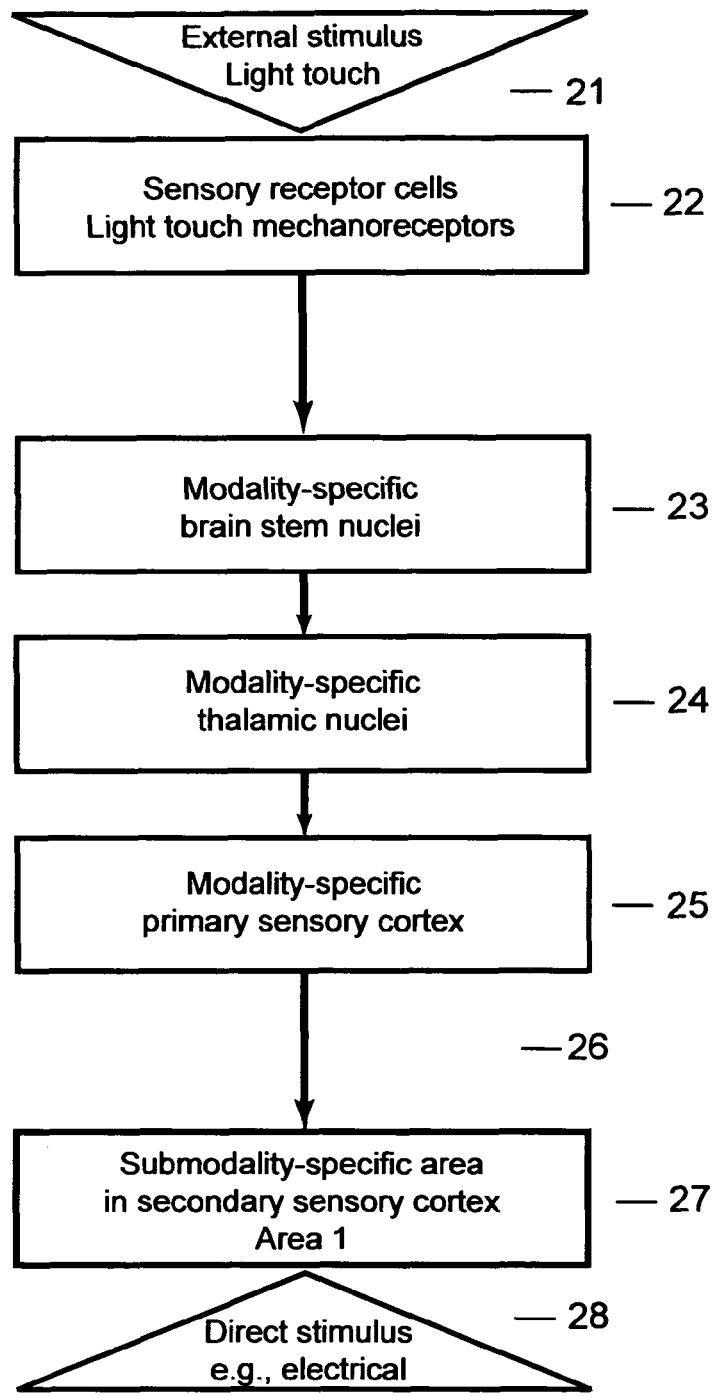
FIG. 2 is a block diagram illustrating information flow from light touch mechanoreceptors in a point of the body surface to Brodmann area 1.

[7.1] External stimuli (FIG. 2). Consider light touch to the right index fingertip, 21. Light touch stimulus activates mechanoreceptors in the fingertip, 22. This stimulation is first projected to the modality-specific brain stem nuclei, 23, and then to the modality-specific thalamic nuclei, 24. The thalamic nuclei project the stimulus to modality-specific primary somatosensory cortex area 3b in the contralateral hemisphere, 25. Then, the stimulus is projected, 26, to the locus-specific cortical columns that represent the right index fingertip in Brodmann area 1, 27, which is a non-primary modality-specific cortical area as defined by the criterion in section C4. The responses to the above stimulation of area 1 cells include:
1) Transient increased activation of area 1 cells representing the right index fingertip
2) The sensation of light touch in that fingertip
3) The correlated voluntary behavioral response signifying the presence of that sensation The inactivation of the area 1 cells that represent the right index fingertip eliminates the above three forms of response, despite the presence of light touch to the right index fingertip, without eliminating responses to stimuli to any other part of the body surface.

[7.2] Direct brain stimulation and intrinsic properties. The direct stimulus (electrical, chemical or magnetic) of area 1 cells that represent the right index fingertip in the left hemisphere, 28, can evoke the sensation of light touch in the fingertip in the absence of external stimulus. The surface area of a cortical column is less than a millimeter, and moving the locus of stimulation by a millimeter can be sufficient to change the locus of the evoked sensation. This fine resolution is also characteristic of subcortical loci. The same type of direct stimulus to area 1 that evokes the sensation of light touch in the right index fingertip could evoke the sensation of a basic color if applied to color submodality-specific area in the visual cortex (area V4/V8), or the sensation of pleasure if applied to the nucleus accumbens. The direct stimulus, other than intensity and duration, does not contribute to the qualitative aspect of the evoked sensation. This qualitative aspect of the evoked sensation is an intrinsic property of the stimulated cells.

[7.3] Endogenous stimuli. Visual sensation while dreaming is an example of endogenous stimuli. Visual dreams activate secondary, but not primary, visual cortical areas. Thus, there is no input from the eyes. The stimulation, therefore, is endogenous. Imagining the color red, for example, induces endogenous stimulation of the color evoking cells in the submodality-specific color area, V4/V8, in the visual cortex. Similarly, imagining sweet taste induces endogenous stimulation of the sweet-evoking cells in the secondary gustatory cortex. These endogenous stimuli can be enhanced by hypnosis. Illusions and hallucinations are other examples of sensations that result from endogenous stimuli of the correlated submodality elements of sensations. Central pain is evoked by endogenous stimuli of brain loci that evoke ordinary pain. Tinnitus is an example of auditory sensations evoked by endogenous stimulation of the secondary auditory cortical areas. Imagining a particular taste, for example, evokes the endogenous activation of locus-specific neurons in the secondary gustatory cortex. Locus-specific neurons that determine the subjective quality of a unitary subjective state may evoke this subjective state by stimulation regardless of its source, whether it is external through sensory receptors, external through direct brain stimuli, or by endogenous stimuli.

[8.] Recapitulation.

[8.1] Sensations are Evoked in the Brain.

[8.2] Unitary Subjective States are Present at Birth Prior to Postnatal Experience.

[8.3] Cells that Determine Subjective States are Locus-Specific

D. Determining Versus Evoking Unitary Subjective States

[1.] Determining vs evoking mental states: an analogy. The focus of the invention is how the intracellular molecular constitution of cell types determines their intrinsic function, in general and of intrinsic function related to unitary subjective states, in particular. There are some additional conditions that must be met in order for an intrinsic function to be realized. An analogy makes clear the distinction between determining and evoking an intrinsic function. Striking a piano key generates air vibration with 1) fundamental frequency, 2) harmonics of that frequency and 3) the characteristic envelope of the harmonics, which constitute timbre. These three properties are intrinsic properties of the string and are thus atemporal. The strength of striking a piano key affects intensity or the amplitude of vibration which correlates with the subjective attribute of loudness. Thus, except for intensity, focus on intrinsic function makes possible the provisional exclusion of both the temporal dimension and the extracellular spatial dimensions. The resonant vibration frequency of a string in a musical instrument, such as the piano, manifests 1) a fundamental frequency, 2) harmonics (integral multiples of the fundamental frequency) and 3) timbre, the spectral envelope and decay of the harmonics and 4) loudness, the amplitude of the harmonics. Other than amplitude, a string determines its intrinsic function. This determination is structural and atemporal. Upon being struck by the piano key that string manifests those intrinsic properties. The vibration of a string is a temporal process. Likewise, the molecular constitution of the cell determines its intrinsic function. A stimulus, such as the binding of a ligand to a receptor, can elicit that intrinsic response. Similarly, brain cells that determine any given unitary subjective state can evoke them upon being stimulated in a conscious subject that attends to the stimulus.

[2.] Intensity. The intensity attribute is applicable to any particular unitary subject state, such as loudness, heaviness and brightness. There are two related mechanisms regulating intensity of awareness: organism-wide and focused. Feeling drowsy, relaxed, tense or alarmed exemplifies general levels of intensity of awareness. Attention, in contrast, provides focused intensity to some aspects, coupled with reduced intensity to other aspects, of awareness.

[2.1] General awareness. A conscious person can be aware of a great diversity of stimuli. Thus it is useful to make the distinction between being conscious or not and between the content of what a person may be aware of. General consciousness, by itself, is devoid of content and may be considered to be background consciousness. This background consciousness is a necessary condition for experiencing any foreground content of awareness. Background consciousness does not contain any smaller constituents and is thus a unitary subjective state. Like any other unitary subjective state, background consciousness is determined and can be evoked by locus-specific cells. The intrinsic function of those cells is determined by their protein specificities.

[2.2] Attention. Attention is serial. Consequently, there are mechanisms that serially shift the spotlight of attention among competing stimuli. Attention increases the intensity of what is within its spotlight and suppresses the intensity of what is outside that focus.

Figure 3:
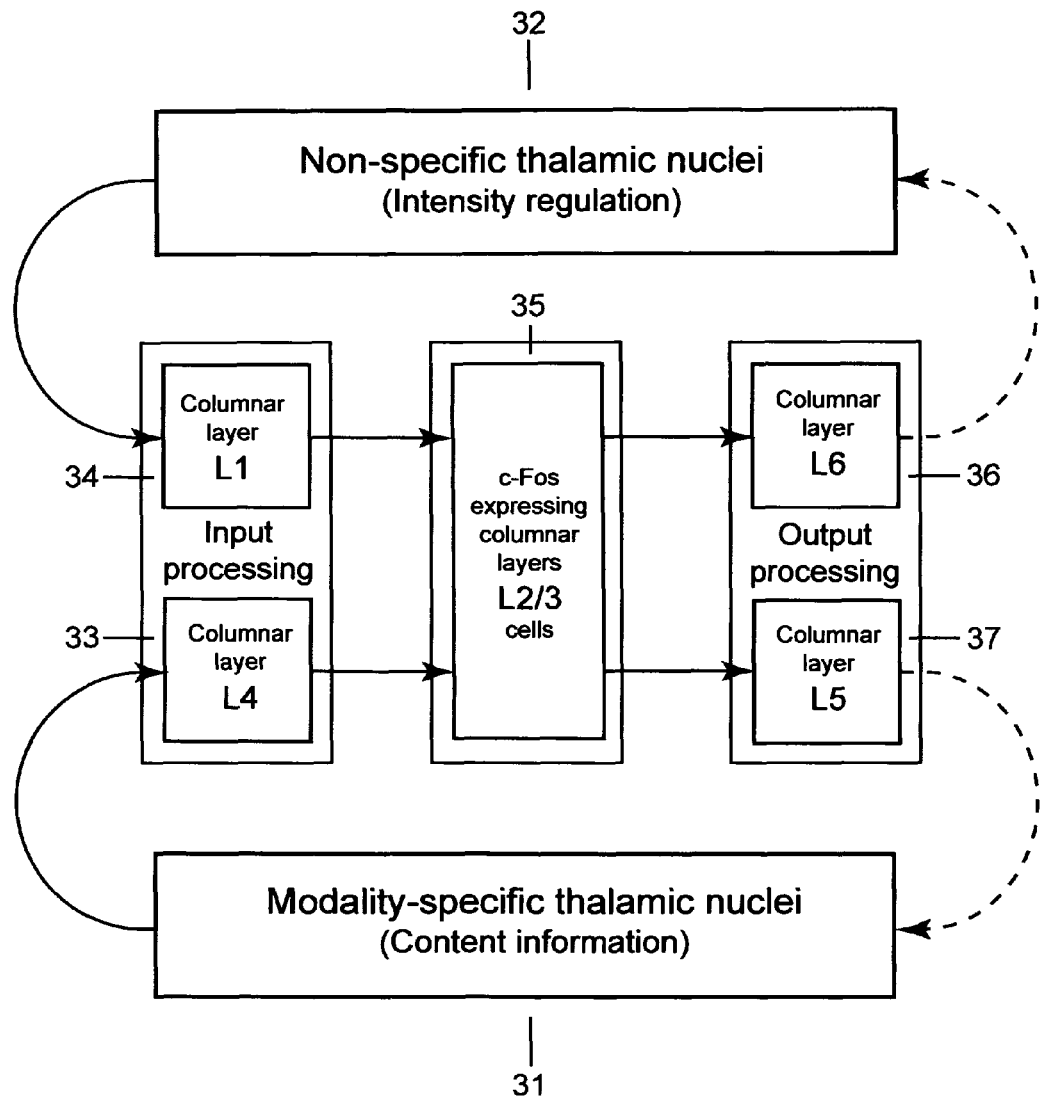
FIG. 3 illustrates the distinction between information and regulation in a subset of feedforward connections to and from c-Fos-expressing layer 2 and 3 cortical cells in response to stimulus typical of a given submodality element of sensation in a cortical column of a submodality-specific area.

[3.] The distinction between information and regulation. FIG. 3 highlights the distinction between content-related and regulation-related input from the thalamus to the sensory cortex. It shows a subset of feedforward projections between the thalamus and a cortical column that determine and can evoke a submodality element of sensation—inter-columnar and reciprocal connections are not shown. In response to stimuli typical of any given submodality element of sensation, cells in layers 2 and 3 of submodality-specific cortical columns express the immediate early gene c-Fos. Modality-specific thalamic nuclei, 31, project content-related information primarily to layer 4 (L4) cells, 33. Layer 5 (L5) cells 37; receive content information from layer 4 cells (as well as from cells in other lamina—not shown). Non-specific thalamic nuclei, 32, project regulatory information primarily to layer 1 (L1), 34. Layer 6 cells (L6) received regulatory input from cells in layers 2 and 3 (and from some other layers—not shown).

E. Phenotype and Protein Specificity of Cell Types

[1.] Phenotype is a Manifestation of the Molecular Constitution of the Cell.

[1.1] The molecular constitution of the cell. The cell type is the basic unit of function and dysfunction. Its molecular constitution contains information about 1) the evolution of the organism, 2) the developmental differentiation of cell types and 3) the intrinsic function of the cell. Much of this information is not obtainable by observing organisms or the phenotypes of cells. A cell's molecular constitution provides a common denominator relative to which any cell type may be specified. Based on phenotype, there are about 220 different cell types in the human body. The olfactory receptor cell is one of these phenotypic cell types. On the basis of molecular constitution, however, olfactory cells have about 370 distinct subtypes in humans. Molecular constitution determines the difference in intrinsic function of among the different olfactory cell subtypes. Neurons and glia are cells. Molecular constitution specifies the difference in the intrinsic function of brain cells.

[1.2] The hierarchical organization of cell types. Cells of the body have a hierarchical organization that reflects their organ, tissue and tissue-specific cell type membership. This hierarchy has a spatial, topological three-dimensional (3D) organization. The 3D distribution of cell types in the body maps organs and tissues including bones, musculature, skin and the nervous system. In the brain said 3D distribution of cell types maps nuclei, subnuclei, and functional neural clusters within nuclei. The hypothalamus, for example, contains nuclei, such as the suprachiasmatic nucleus, which contains clock neurons that regulate the circadian rhythm. In the cerebral cortex, for example, this hierarchical organization is manifested by modality-specific areas, which contain submodality-specific areas, which finally contain cortical columns representing submodality elements of exteroreceptor-based sensations. These submodality-specific areas contain cortical columns, which determine the qualitative aspects of subjective states that do not contain smaller constituents. The top-down three-level hierarchical organization of sensory modalities, submodalities and submodality elements of is spatially represented in the cortex in an outside-in fashion.

F. Some Aspect of Cellular Function

[1.] The Response of Cell to the Binding of a Ligand is Cell-Type-Specific

[1.1] Homeostatic mechanisms and input-independent output The function of the cell's homeostatic mechanism is a defining attribute of life. When a cell's available energy falls below a certain set-points, homeostatic mechanisms trigger that cell's action on the environment. This action constitutes cellular output, which is independent of input. Put differently, the output of the cell is not computable from its inputs. For example, clock neurons in the suprachiasmatic nucleus of the hypothalamus, produce circadian cycle-related output even in vitro.

[1.2] Cell-type-specific response. With the exception of mutagens and retroviruses, the DNA and gene expression mechanisms of cells are innate. Any mature cell is the result of these gene expression mechanisms' response to external cues. The molecular constitution of any cell type combines attributes that are innate with attributes resulting from the operation of innate mechanisms. This molecular constitution is the basis for the cell-type-specific response of neurons and glia. Action potentials, for example, cause the release of neurotransmitters from axon terminals of a presynaptic neuron. With the exception of gapjunctions, these action potentials do not reach the postsynaptic neuron. Thus, these action potentials are a distal cause of the postsynaptic response. The neurotransmitter released from the presynaptic axon terminals is likewise a non-proximate cause of the postsynaptic neuron response. Such neurotransmitters can be replaced by binding to the postsynaptic receptor of different agonist molecules. More generally, the molecular constitution of the cell mediates the effects of the environment. Molecular constitution determines intrinsic cell-type-specific function.

[2.] Addressing complexity. The complexity of the phenomena under investigation is reduced by 1) focus on common denominators, 2) the removal of intervening variables and 3) the distinction between proximal and distal causes. This approach is reflected in the invention as follows:

[2.1] Intrinsic function. Structure determines function. This is true for an individual molecule, as well as for the molecules constituting the cell. While cellular function is temporal, structure is not. Thus, the study of structure makes it possible to study intrinsic function with the provisional exclusion of the temporal dimension.

[2.2] Gene expression. The initial response of a cell to external stimuli takes a fraction of a second. Such response-time pertains to events such as seeing a light flash or hearing a buzzer. In contrast, the expression of immediate early genes takes one or two orders of magnitude longer and that of cell-type-specific genes take longer still. Thus, gene expression is a distal cause of cellular response. The invention provisionally excludes this distal causal factor.

[2.3] Dysfunction is best investigated indirectly. There are a few ways for a cell to function normally and a multitude of ways for it to fail. This asymmetry is the result of the fact that many cellular functions are conjunctive, and a dysfunction of one molecule can eliminate the joint function. If the number of functioning proteins acting together is just twenty, then the number of possible combinations of dysfunction exceeds one million ($2^{20}$). The number of error-correcting proteins in the cell, for example, is in the hundreds. The implied combinatorial explosion makes it suboptimal to study dysfunction directly. For this reason the focus here is on normal function to form a basis of diagnosing dysfunction as a departure from that normal function.

G. Molecular Cytoarchitecture

[1.] Heuristic Characterization of Cell Types.

[1.1] Some current characterizations of cell types. A cell type is commonly characterized by the subset of genes that may be expressed in it or in terms of the proteins that are actually expressed in it. Both characterizations include transiently-expressed proteins and housekeeping proteins. These characterizations obscure what is unique about any given cell type. Cell type identity is maintained while proteins are transiently expression and degraded. Housekeeping proteins are expressed in all cell types and in this sense they are not cell-type-specific.

[1.2] Defining cell types by their protein specificities. A cell type is here heuristically defined by its continuously, or constitutively-expressed proteins. Hereafter, this definition of a cell type is referred to as its protein specificity. As explained below, housekeeping proteins are included in said characterization in a separate group.

[2.] Protein specificity of cell types. These proteins reflect the hierarchy of organ, tissue, and tissue-specific cell types. These proteins form a hierarchy, which uniquely characterizes any cell type of in any given organism. At the bottom of this hierarchy are proteins that are found in all cell types (i.e. housekeeping proteins). At the top of the hierarchy are proteins that are unique to any one cell subtype relative to any other subtype of the same cell type.

[3.] Cytoarchitecture. Cytoarchitecture, the cell type distribution in the brain, identifies ganglia, nuclei, subnuclei and cortical areas by cell type distribution. Cytoarchitecture is a gross manifestation of the underlying protein specificity of these brain cells. The 3D topological distribution of constitutively-expressed cell-type-specific proteins would map intrinsic function with extremely high resolution. It would also reflect the gross mapping of phenotype-based cytoarchitecture.

[3.1] Brodmann areas. The differential distribution of cell types among the six cortical layers is the basis for dividing the cerebral cortex into Brodmann areas. This cell type distribution identifies, for example, the primary visual cortex (area 17), the primary auditory cortex (area 41), and the primary motor cortex (area 4).

[3.2] Molecular cytoarchitecture. The cytoarchitecture of Brodmann areas identifies functional cortical areas without any reference to either interactivity or connectivity. The invention, similarly, identifies functional areas without any reference to either interactivity or connectivity. There are, however, two differences: 1) the invention provides sub-cellular resolution, and 2) the methods of the invention are not limited to the cerebral cortex (or to the brain).

[3.3] Cytoarchitecture can identify cells that determine and can evoke subjective states. Area 1 in the somatosensory cortex is submodality-specific area for light touch and is located in the non-primary somatosensory cortex (see Section C3 above). Cortical columns that represent the fingertip of the right index finger in area 1 determine the quality of the sensation of light touch in that finger. These columns evoke the sensation of light touch in the fingertip of the right index finger when stimulated in a conscious person. Such stimulation can be an actual touch, direct external stimulation (e.g. electrical) or endogenous stimulation (e.g. hallucination). The reversible inactivation (e.g. by cooling or a local application of Lidocaine) selectively eliminates light touch sensation in the corresponding point on the body surface. There is no other location in the brain (e.g. area 3b or area 2) where the selective inactivation criterion applies. The surface of the body is spatially represented in area 1. Thus, the submodality of sensation of light touch is a common attribute that is identified by the cell type distribution of area 1.

H. The Hierarchy of Cell-Type-Specific Proteins

Figure 4:
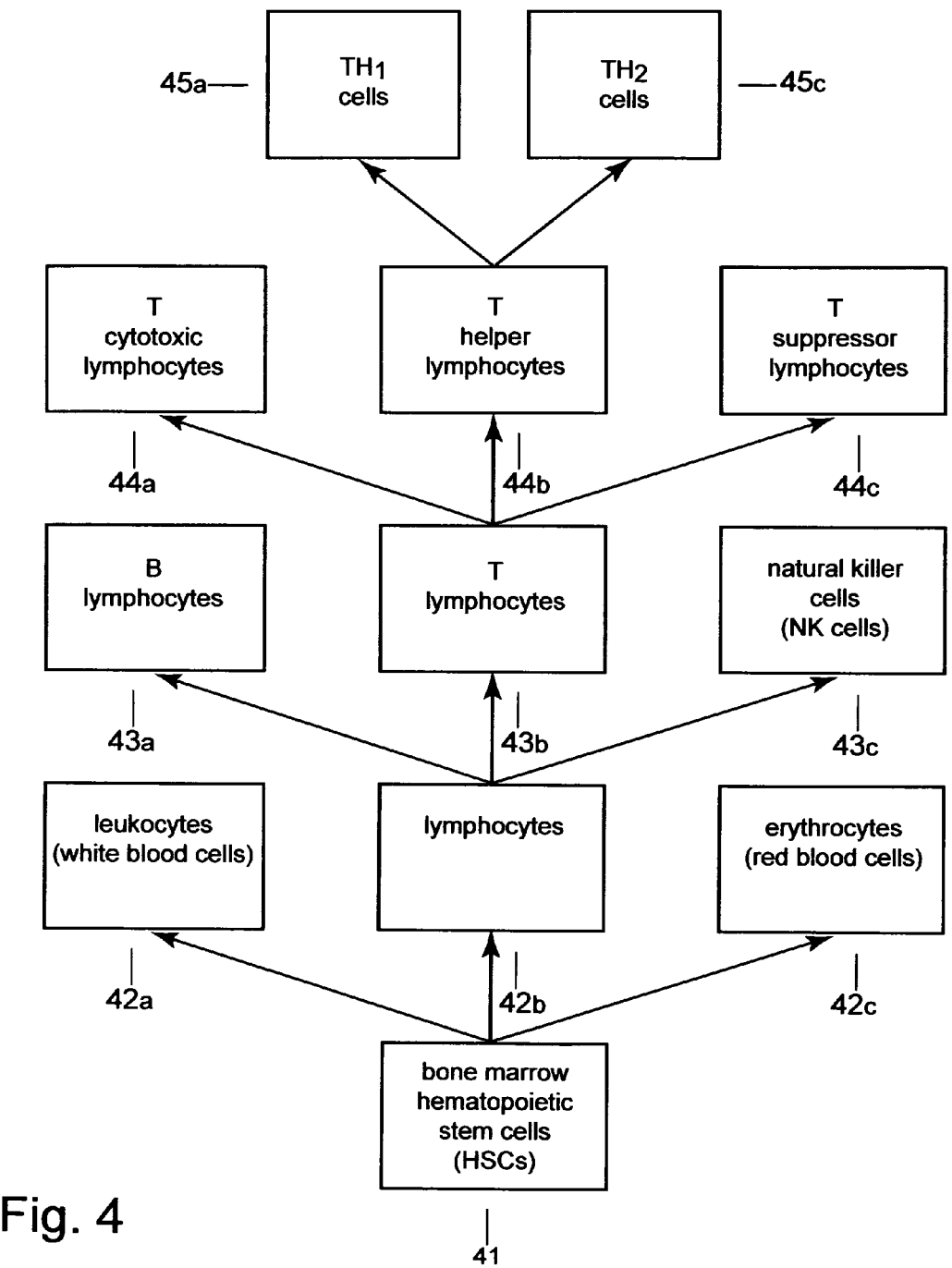
FIG. 4 illustrates the hierarchical organization of cell types and subtypes in reference to lymphocytes.

[1.] Hierarchy of cell types and subtypes. Consider lymphocytes, for example. FIG. 4 shows cell types and subtypes of lymphocytes. Bone marrow hematopoietic stem cells (HSCs), 41, give rise to leukocytes (white blood cells), 42a, lymphocytes, 42b, as well as erythrocytes, (red blood cells) 42c. The three basic types of lymphocytes are B lymphocytes 43a, T lymphocytes, 43b and NK cells 43c. The three basic types of T lymphocytes are T cytotoxic lymphocytes, 44a, T helper lymphocytes, 44b, T suppressor lymphocytes, 44c. The two types of T helper lymphocytes are the TH1 cells, 45a, and the TH2, cells 45b. The four stages of cell differentiation of the hematopoietic stem cells into either TH1 or TH2 lymphocytes involve changes in the hierarchy of the constitutively-expressed proteins of those cell types. The protein specificity of the TH1 and TH2 cells reflect their membership in 1) lymphocyte cells, 2) T lymphocyte cells and 3) and helper T lymphocyte cells.

Figure 5:
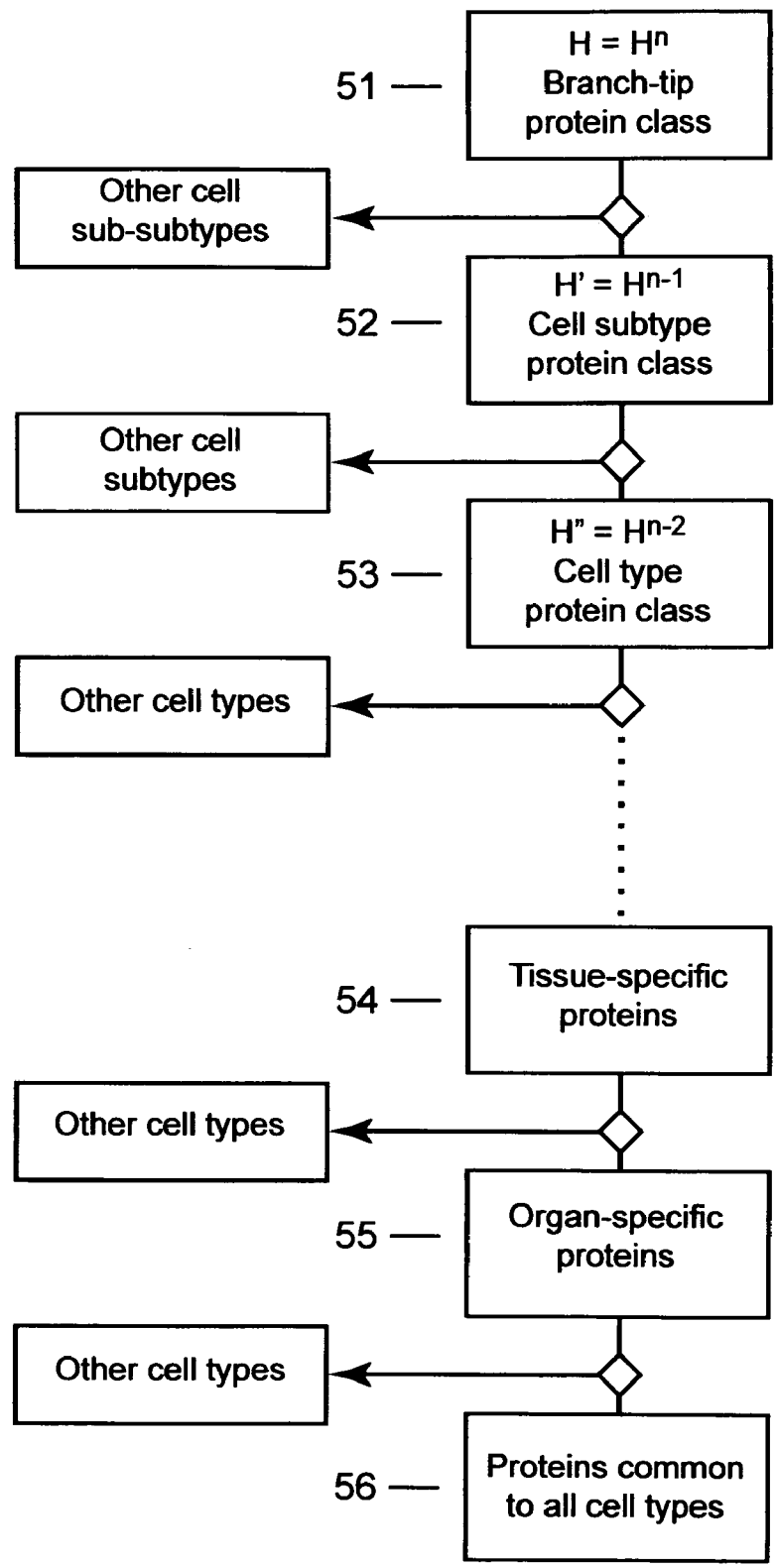
FIG. 5 is a generalized representation of the hierarchy levels of cell-type-specific constitutively-expressed proteins.

[1.] The hierarchical organization of protein classes that characterize cell types. FIG. 5 illustrates any cell as a hierarchy of its cell-type-specific constitutively-expressed proteins. It is convenient to view this hierarchy as a tree. The trunk of the tree, 56, consists of proteins that are found in all cell types of an organism (e.g. actin and mitochondria-related proteins). In the next level, 55, are organ-specific proteins and proteins that are found in many but not all cell types. The next higher level, 54, contains tissue-specific proteins and other proteins with a more restricted cell-type distribution.

Figure 6:
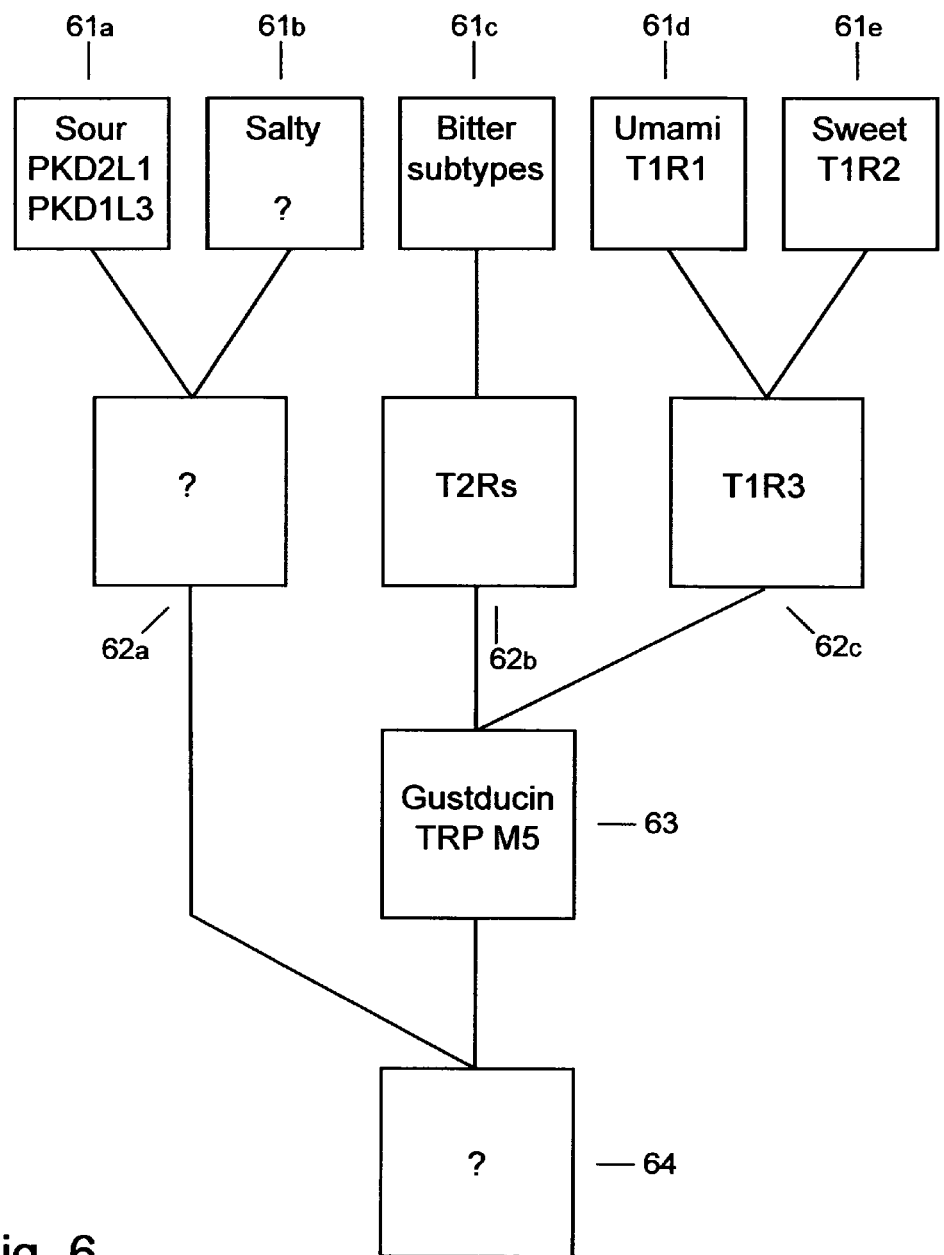
FIG. 6 illustrates the hierarchical constitutively expressed proteins in some taste receptor cells in the tongue.

[1.1] A top-down characterization of cell types. A top-down characterization of three or four hierarchy protein levels provides an abbreviated characterization of cell types in an organism. Any cell type that has no subtypes represents a branch-tip of the tree. Let H designate hierarchy, and let the superscript designate hierarchy level from the tree-trunk. Then the branch-tip protein level may be written as $H^n$, 51, and the next level down, level $H^{n-1}$, 52, the third level down, as $H^{n-2}$, 53, and so on. FIG. 6 shows hierarchy level of some constitutively-expressed proteins in taste receptor cells of the tongue in a top-down sequence. The proteins PKD2L1 and PKD1L3 characterize the sour taste receptors in the tongue, 61a. The salty taste receptor cell, an ion channel, has not yet been finally characterized, 61b. There are over twenty bitter subtype receptors, 61c. The T1R1 protein is specific to umami taste receptors, 61d, and T1R2 protein is specific to sweet taste receptors, 61e. It is not yet known if there are proteins common to salty and sour taste receptors, 62a. T2Rs is the taste receptor protein common to all bitter subtype receptors, 62b. The T1R3 protein is common to umami and sweet taste receptor cells, 62c. Gustducin, Trpm5, PLCbeta2 and IP(3)R3 (type 3 isoform of inositol 1, 4, 5 trisphosphate receptor) are members of a class of proteins that are common to bitter, sweet and umami taste receptors, 63. The taste receptor proteins that are common to all five known taste receptor cells has yet to be identified, 64.

The sweet and umami taste receptors are here characterized in terms of three-level hierarchy. Thus, said two taste receptor types can be specified in terms of a three-level hierarchy as follows:

Umami taste receptor cells: [Gustducin & Trpm5 & PLCbeta2 & IP(3)R3] & (T1R3) & (T1R1)

Sweet taste receptor cells: [Gustducin & Trpm5 & PLCbeta2 & IP(3)R3] & (T1R3) & (T1R2)

This three-level hierarchy characterizes taste receptors in a top-down fashion, without specifying proteins that are common to all five taste receptor types. Let K", K' and K designate respectively these three hierarchical levels where K" is the most common and K is the most specific. Then, schematically, these receptor proteins can be written as K" & K' & K1 and K" & K' & K2. The hierarchical level of proteins can be represented in a bottom-up or top-down sequences. The bottom-up sequence includes all constitutively-expressed proteins in a cell. The top-down characterization of cell type can be limited to the smallest number of levels that uniquely identify a cell type. Three or four levels are typically sufficient to uniquely characterize a cell type. In some cases, such as photoreceptor cells and olfactory receptor cells, the top-level protein uniquely characterizes a cell type.

[2.2] The notion of the protein class. The K" level proteins Gustducin and Trpm5 are common to bitter, umami and sweet taste receptors. Said proteins exemplify the fact that a hierarchical level can be occupied by more than one protein. In the tongue the proteins PKD2L1 and PKD1L3 are K level proteins that are specific to sour taste receptors. The inactivation of either eliminates the function of sour taste receptors. Such conjunctive function is typical of proteins that share the same hierarchy level. The protein, or proteins, that constitute a hierarchy level are here called a 'class'. The inactivation of any member protein eliminates the function of that class. Thus, a cell type is characterized by a hierarchy of constitutively-expressed protein classes. At the base of such hierarchy are the housekeeping proteins that are found in all cell types and at the apex of the hierarchy are protein class that are unique relative protein classes of other cell types that share the same proximate node.

[2.3] A tree representation of the hierarchy of protein classes. The hierarchy of protein classes in cell types of an organism is visualized by a tree. The hierarchical levels of other proteins involve sorting proteins by their organ, tissue and tissue-specific cell type commonalities. The result of such sorting yields the tree-trunk proteins that are common to all cell types in an organism. Moving up from the tree-trunk to the lower branch-nodes reflects the decreasing number of organs in which a given protein is found. The next group of branch-nodes reflects the decreasing number of tissues types in which any protein is present. Then, the higher group of branch-nodes reflects the decreasing number of tissue-specific cell types in which any given protein is found. Any branch ends either with a branch-node or a branch-tip. A branch-tip signifies that the cell has no further subtypes. The sequence of protein classes that characterize a cell type is unique. Such sequence is represented by the unique branching pattern from the tree-trunk to a particular branch-tip. The number of branch-tips on this "tree" is the number of cell types in a given organism.

[2.4] Relatively unique characterizations of cell types. Proteins that have the same proximate branch-node are unique relative to each other. Consequently, branch-tip proteins that have the same proximate branch-node are unique to each other. Thus, if K' & Ki and K' & Kj are any two branch-tip proteins then i≠j. These branch-tip proteins remain unique relative to each other as the next proximate branch node is added. Thus, K" & K' & Ki is unique relative to K" & K' & Kj. The conjunction of a tissue-specific protein with branch-tip protein can provide another level of unique characterization. The KD2L1 and PKD1L3 proteins are found in sour taste receptors and in the gut. With the identification of tissue-level proteins that are common to the different taste receptor cells their conjunction with KD2L1 and PKD1L3 would constitute a unique characterization of the sour taste receptor.

[2.5] Scope of inactivation. 1) The inactivation of a protein eliminates the function of its class (heterogeneity of effects). 2) The inactivation of a branch-tip protein selectively eliminates the function of its cell without eliminating the function of cells with other branch-tip proteins with the same proximate branch-node. 3) The inactivation of a protein class eliminates the function of all cell types containing that class.

I. Identification by Activation and Validation by Inactivation

[1.] Stimulation of cells that determine unitary subjective states. Brain cells that determine any given unitary subjective state can evoke that sensation in a person who is conscious and attends to the stimulus (i.e. that attention is not diverted elsewhere). Such stimulation has diverse manifestations that include:

[1.1] Corresponding locus-specific cells manifest transient increased activation

[1.2] A conscious person experiences that submodality element of sensation

[1.3] That person exhibits a behavioral response signifying the presence of that sensation

[2.] Inactivation of cells that determine a submodality element of sensation. The inactivation of such locus-specific cells has the following consequences:

[2.1] The three responses listed above (1.1, 1.2 and 1.3) are eliminated

[2.2] Responses to stimuli of other elements within the same submodality remain unaffected

[3.] Responses to stimuli specific to a given submodality element. The increased activation of locus-specific cells (see 1.1 above) has diverse responses that can include the following:

[3.1] Increased evoked potential activity

[3.2] Increased utilization of glucose and oxygen

[3.3] Increased regional blood flow

[3.4] Increased expression of immediate early genes

[3.5] Increased expression of cell-type-specific genes

[3.6] Plasticity change resulting in the increased number of the particular cell type

[4.] Selective inactivation. The function of these cells can be inactivated by:

[4.1] Preventing transcription of a particular protein (modifying chromatin methylation)

[4.2] Preventing translation of an expressed protein mRNA (using RNA interference)

[4.3] Preventing protein function (using antibodies against cell-surface proteins).

[5.] Plasticity. Persistent stimulus over an extended period of time causes an increase in the number of cells of the type that is stimulus-specific and a corresponding decrease in related adjacent cells. This process involves a change in the protein specificity of related nearby cells so as to become stimulus-specific. Such plasticity change is also manifested in cases of extended absence of a particular stimulus. For example, persons with mutated long wavelength photoreceptor cells have depleted representation of red-specific cells in color submodality area V4/V8 of the visual cortex. Thus, the red-specific cell type in visual area V4/V8 of the visual cortex is identifiable by contrasting a tissue sample from a person who had normal color vision with a tissue sample from a person who was red-blind.

[6.] Proving a Causal Connection Between the Mental and the Physical.

[6.1] A procedure to establish behavioral responses to signify the presence of subjective states. Using techniques of psychophysics, a one-to-one correspondence is established between 1) submodality elements of sensation and external stimuli and then 2) between these elements of sensation and voluntary behavioral responses and therefore 3) between the external stimuli and their corresponding behavioral responses. As a result, the response following a characteristic stimulus signifies the presence of a particular element of sensation while the absence of the response following its stimulus signifies the absence of the sensation. This procedure is the basis for using publicly observable responses as manifesting subjective states that are not publicly observable.

[6.2] Identification by preferential activation. In each cerebral hemisphere, cells that determine any unitary subjective state are locus-specific. Such a unitary subjective state can be evoked in response to external stimuli, direct stimuli or endogenous stimuli. Upon stimulation the locus-specific cells manifest preferential activation that is the basis for their initial identification. Activation, especially if persistent, elicits gene expression in the stimulated cells. Immediate early genes (IEGs), which are transcription factors, are expressed first. The IEG c-Fos is one of the IEGs that are expressed in cells that determine unitary subjective states. In secondary modality-specific cortical areas c-fos is expressed in columnar layers 2 and 3 with maximal expression level about two hours after stimulation. After several days the stimulated cells would contain cell-type-specific mRNA and proteins. Such activation proves correlation between the stimulus and the c-Fos expressing cells, but correlation does not prove causation.

[6.3] Validation by selective inactivation. Inactivating cells were identified by activation is the basis for validation. Inactivation a protein can eliminate the function of cells containing it. One method of inactivating a protein involves the use of the RNA interference (RNAi) mechanism, which prevents translation of its expressed mRNA. This method uses replication-deficient lentivirus as a vector to deliver to brain cells an antisense sequence of the target mRNA. The antisense RNA binds and degrades the target mRNA thus presenting its translation into protein. Identified cells are validated if their inactivation selectively eliminates the correlated behavioral response without eliminating responses to stimuli of other elements within the same submodality. This selective inactivation proves causal connection between any given submodality element and its corresponding locus-specific brain cells.

[6.4] Application to unitary subjective states other than exteroreception. Like exteroreception, all subjective states are spatially and hierarchically represented in the brain. The logic of preferential activation and selective inactivation applies to cells that determine any of these unitary subjective states.

[7.] An identification sequence for the locus and protein specificity of cells of interest. The identification follows an outside-in (or top-down) sequence: sensory modalities are identified first. Next, submodalities are identified within their respective modalities. Then, locus-specific cells that determine submodality elements of sensation are identified.

[8.] Plasticity. Developmental history can affect the locus of cells that determine unitary subjective state. Such developmental history can change lateralization. Underdevelopment of the cerebral cortex can result in having sensations determined by cells located in subcortical loci. These changes in the locus of cells that determine sensation provide opportunities for identifying their protein specificities.

Part II Methods

J. Overview

Figures 7A, 7B:
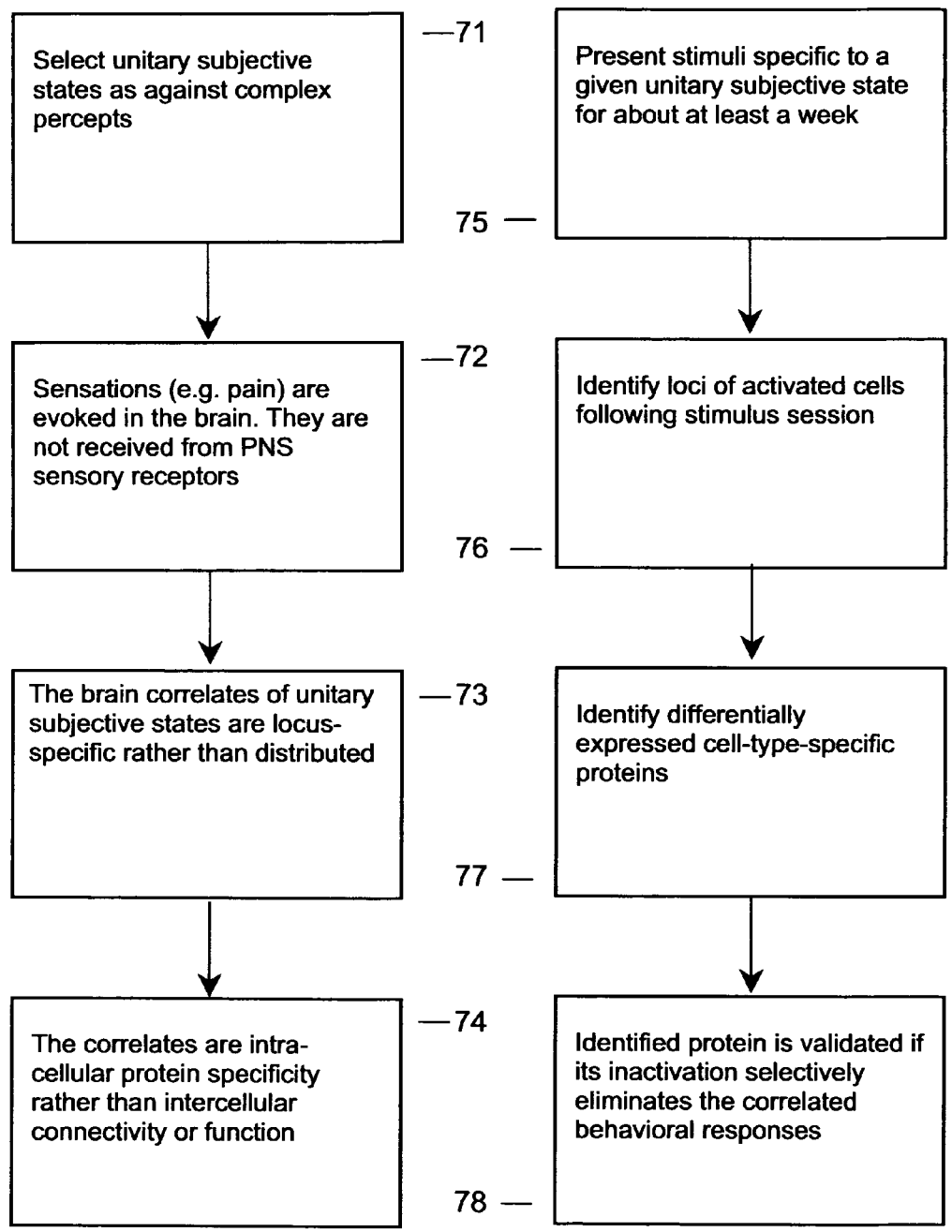
FIG. 7a is a block diagram of main stages of the virtual identification of proteins of interest.
FIG. 7b is a block diagram of main stages of the actual identification of proteins of interest.
Figure 8:
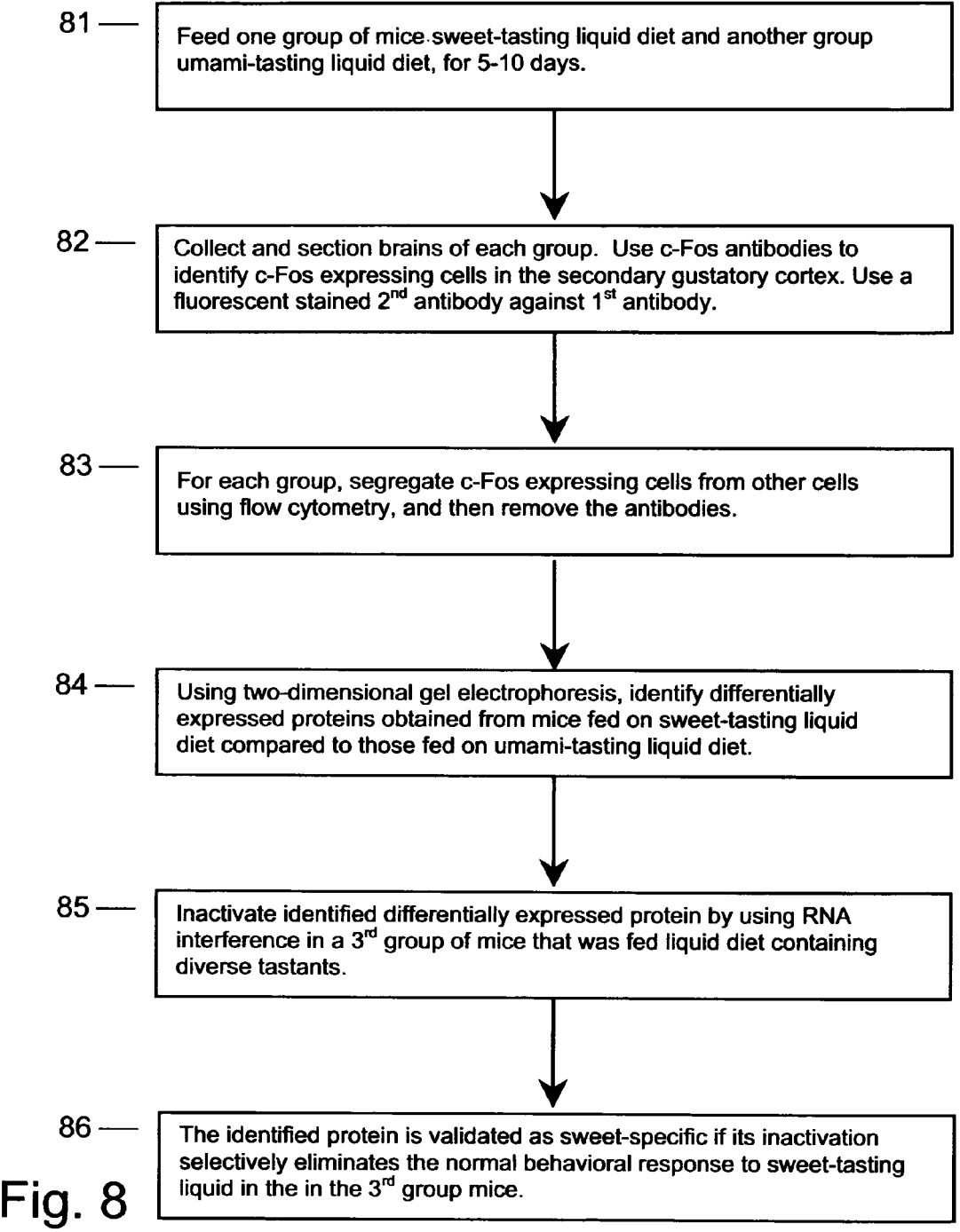
FIG. 8 illustrates an application of the method for identifying of proteins specific to cells in the secondary gustatory cortex that determine and can evoke the unitary subjective state of sweet taste using one of available alternative techniques.

[1] Virtual and actual identification of neural correlates of consciousness (NCC). FIG. 7a is a block diagram of the main stages of the virtual identification of NCC. FIG. 7b is a block diagram of the main stages of the actual identification. FIG. 8 is an example of the combination of the virtual and actual identification as applied to a particular unitary subjective state.

[2.] Virtual Identification—FIG. 7a.

71 Unitary subjective states. The first identification stage is the selection of a subjective state, such as thirst, which does not contain smaller constituents, but not a subjective state such as hunger, which may contain subtypes specific to glucose, carbohydrates fats and proteins.

72 All subjective states are evoked in the brain. The second stage locates the cells that determine and can evoke any given unitary subjective state (e.g. pain) in the CNS and not in the peripheral nervous system.

73 Localization. The third stage identifies intrinsic function of any cell with its locus rather than attributing that function to multicellular distributed network.

74 Intracellular molecular constitution. The fourth stage identifies intrinsic function of any cell with its hierarchy of constitutively-expressed proteins.

[3] Actual Identification—FIG. 7b.
75 Stimulus. Use genetically identical model animals. For a period of at least five days, present a test group with stimuli specific to a given unitary subject state. At the same time, present a control group with stimuli excluding the one specific to the one presented to the test group.
76 Localization. Identify loci of cells that are activated in the test group but not in the control group.
77 Identify differentially expressed proteins. Identify locus-specific and cell-type-specific constitutively-expressed proteins in the test group but not in the control group.
78 Validation of identification. Inactivate identified protein in a third group of model animals. Provide animals with diverse, closely related stimuli, including the one for the unitary subjective state of interest. Identification of a protein is validated if its inactivation selectively eliminates the normal behavioral response to the typical stimulus

[4.] An illustration of the identification method using mice—FIG. 8. FIG. 8 is a block diagram of the application of the method for the identification of a particular unitary subjective state—the submodality element of the sensation of sweet taste. The method is applicable to any submodality element of sensation. Genetically homogenous mice are reared, to the extent feasible, in similar conditions. The maximal response to stimuli is obtained during the postnatal critical period. The method below is exemplified by reference to the sweet and umami tastes. The method illustrated is applicable to any submodality element of sensation. The major identification stages are first summarized in the FIG. 8 flowchart, and then are described in greater detail. The main stages are:

81 Stimulation. Feed one group of mice a sweet-tasting liquid diet, and another group an umami-tasting liquid diet, for 5-10 days.
82 Identifying responsive cells in submodality-specific cortical area. Collect and section brains of each group. Use c-Fos antibodies to identify c-Fos expressing cells in the secondary gustatory cortex. Use a fluorescent stained $2^{nd}$ antibody against $1^{st}$ antibody.
83 Segregating responsive cells from others. For each group, segregate c-Fos expressing cells from other cells using flow cytometry and then remove the antibodies.
84 Identifying differentially-expressed cell-type-specific proteins. Using two-dimensional gel electrophoresis, identify differentially expressed proteins obtained from mice fed on sweet-tasting liquid diet compared to those fed on umami-tasting liquid diet.
85 Inactivation of identified protein. Inactivate identified differentially expressed protein by using RNA interference in a $3^{rd}$ group of mice that was fed liquid diet containing diverse tastants including sweet-tasting liquid diet.
86 Validation. The identified protein is validated as sweet-specific if its inactivation selectively eliminates normal behavioral response to sweet-tasting liquid in the $3^{rd}$ group mice.

[5.] The difference between methods and techniques. The invention provides methods for the identification of brain loci and the protein specificity of cells that determine and can evoke unitary subjective states. These methods can be implemented by using alternative techniques. Techniques change rapidly. Last decade, for example, activated cells in the brain were often identified by using methods of neuroscience such as 2 deoxyglucose (2-DG) and voltage sensitive dyes. Currently, the use of antibodies against immediate early genes is an effective technique. In the next decade, the predominant technique will involve the operation of databases. The invention does not introduce new techniques and does not depend on the use of any particular technique. The techniques used below to describe the method are used by way of example. The description is sufficient for persons skilled in the art to choose from available techniques those that suit the purpose at hand.

K. Main Identification Stages

[1.0] Alternative identification methods. There are alternative methods for the identification of the protein specificity of the cells of interest.

[1.1] Outside-in identification sequence. The three-level hierarchy of sensory modalities, submodalities and submodality elements exemplifies a top-down sequence. Generally, the top-down identification sequence is simplest. In the case of exteroreception, for example, the cortical regions of most modality-specific areas and some submodality-specific loci are known. Thus, the identification of loci and protein specificities of any submodality element is made relative to its submodality and other elements in that submodality.

[1.2] Data mining. The application of the invention to extant data can result in identification of the brain loci or also the protein specificities of cells that determine and can evoke a given unitary subjective state. Actual identification is embarked upon when data mining does not yield the needed information.

[1.3] Using non-human subjects. The mouse and the rat are used when ever possible for identification of the cells of interest. Non-human primates are used when the subject of interest are unitary subjective states, such as color vision, that are generally lacking in rodents. In addition, non-human primates are used to validate findings in rodents.

[1.4] Use human brain tissue samples. DNA and protein microarrays can be used to identify cells and proteins of interest from human brain tissue samples. Such samples are particularly useful when they are of persons who had congenital absence of a particular subjective capacity (e.g. color blindness or congenital insensitivity to pain).

[1.5] Validation. Cell-type-specific proteins that are identified by any of the main alternative methods are validated by reversible down-regulation in non-human primates. Then they are tested on humans of one particular haplotype group.

[1.6] Updating cell-centered database. The systematic application of the invention would form a database of locus-specific and cell-type-specific hierarchy of constitutively-expressed proteins of cells that determine and can evoke unitary subjective states.

L. Extant Data

[1.] Extant scientific literature. Current scientific literature reflects the dominant intellectual tradition that 1) sensations originate from sensory receptors in the PNS and are "represented" in the brain; 2) subjective states, such as fear or joy, are deemed to be a non-localized or distributed property and 3) intercellular factors account for neural function rather than intracellular molecular factors. The invention, in contrast, locates cells that determine a given submodality element of sensation in the corresponding submodality-specific cortical area of each cerebral hemisphere. Said areas are located within secondary modality-specific areas. Furthermore, said cells evoke said sensation upon being stimulated in a conscious person who attends to the stimulus. The invention can identify said cells from extant data. Here are six examples:

[1.1] Light touch. Section B provides empirical grounds for considering Brodmann areas 1 and 2 non-primary modality-specific parts of the somatosensory cortex SI. Light touch to any point on the body surface, such as the right index fingertip, is represented by area 1 cells in the contralateral cortical hemisphere. The direct stimulation of said cells in the absence of external stimulus also causes said sensation in the right index fingertip. The reversible inactivation of said cells selectively eliminates said sensation despite the presence of external stimulus. Said inactivation is selective in not eliminating responses to stimuli on any other part of the body surface. Thus, said cells satisfy the selective inactivation criterion as being those that evoke the sensation of light touch in any given point on the body surface.

[1.2] Basic tastes. The secondary gustatory cortex is located in the caudolateral prefrontal cortex (clPFC). It contains cells whose response is narrowly tuned to stimuli by basic tastants The invention identifies locus-specific cells in secondary sensory cortices as those that determine and can evoke submodality elements of sensations and thus denies that that the sensation of taste are received from the taste receptor cells in the tongue. The identification of cells in the clPFC as those that evoke sensation of one of the basic tastes needs validated by the selective inactivation test.

[1.3] The auditory sensation of pitch. Cells were recently identified in the secondary auditory cortex that are preferentially activated when experiencing the so-called "missing fundamental" illusion. Normally, when a musical note is played, its fundamental frequency is associated with harmonics or overtones. Playing the harmonics without the fundamental frequency produces the illusion of hearing the missing fundamental. The invention specifies that 1) the sensation of sound is evoked in the secondary auditory cortex and thus is not a property of air vibration or a sensation that is received from the ears, 2) cells that evoke an illusion (in response to endogenous stimuli) are those that evoke that sensation normally in response to stimulus from sensory organs. The invention therefore identifies the cells that are preferentially activated in experiencing the missing fundamental illusion are those that evoke that sensation in normal hearing.

[1.4] Pleasure. A pleasure-related locus of about one cubic millimeter was recently found within the rostral and dorsal quarter of the medial shell of nucleus accumbens. Cells of said locus are activated by the binding of mu-opioids. The sensation of pleasure, or liking, is associated with sweet taste and some other stimuli. Said sensation of pleasure is separable from food intake behavior and also from need/want behavior. The invention provisionally identifies said neurons as those that determine and can evoke the correlated sensation of pleasure. Such identification will be validated if the inactivation of said neurons selectively eliminates that pleasure. Unitary subjective states are determined and evoked by locus-specific neural clusters. The hedonic locus in the nucleus accumbens is connected with a locus in the ventral palladium. But said connection is dissociable.

[1.5] Visual sensation of motion-direction. Visual area V5/MT has been identified as containing cells specific to motion-direction. Said cells are part of eight types of motion direction columns (up, down, right, left and the four diagonal directions). In response to external stimuli of motion-direction in part of the visual field, columns representing said motion-direction in said part of the visual field are preferentially activated. The direct stimulation of direction-specific columns elicits a behavioral response indicating visual sensation of motion in said direction. The inactivation of all columns of the direction creates motion blindness in said direction. The application of the conceptual framework of the invention identifies said cells as those that determine and can evoke the sensation of visual motion in one of said eight directions.

[1.6] The visual sensation of brightness. Recently, neurons in visual area V2 (Brodmann area 18) were identified as selectively correlated with the cornsweet brightness illusion. The conceptual framework of the invention makes explicit that brain cells that evoke an illusion in response to an endogenous stimulus are those that evoke that type normally in response to external stimuli (Section A5.3). Hence, the neurons in visual area 18/V2 that generate the cornsweet brightness illusion are those that determine the qualitative aspect of brightness. Upon stimulation in a conscious person who attends to the stimulus, those neurons evoke sensation of brightness. Brightness relates to the sensation of light. Thus, visual are V2 contains neurons that determine the qualitative aspect of the sensation of light. These neurons evoke the sensation of light upon being stimulated in a conscious person who attends to the stimulus. There is evidence indicating that cells that determine and can evoke the sensation of light are not confined to visual area V2. The above identification would be validated if inactivating proteins specific those neurons produce complete blindness.

[1.7] Validation and correlates on the sub-cellular level. The above six examples identify locus-specific brain cells that determine and can evoke unitary subjective states. The locus identification of said cells is then followed by identification and validation of their protein specificities.

[2.] From DNA and protein databases to cell-centered databases. The systematic application of the invention would result in a cell-centered database. In such a database 1) all cells are of haplotype-specific person or organism of another species, 2) any cell type is specified in terms of its hierarchy of constitutively-expressed proteins, 3) the gene isoform of any protein is associated with each such protein and 4) cell-type-specific expression of housekeeping protein would be included.

M. Using Non-Human Model Animals

[1.] The mouse or the rat as experimental subjects. The use of noninvasive imaging techniques and of human brain tissue sample reduces the dependence the use of invasive methods in non-human model animals. At present, the mouse and the rat are still the first stage in identifying cell-type-specific proteins in humans.

[3] Inducing immediate early genes and cell-type-specific proteins. Mice of the same age are divided in two groups. One test group is fed liquid glucose and the other is fed liquid nourishment with monosodium glutamate (MSG) taste. The brain loci of interest are cortical columns within the secondary gustatory cortex. The taste-specific feeding induces c-Fos expression (in layers 2/3) which is at its maximum about two hours after the stimulus (feeding) session. C-Fos, like all immediate early genes, is a transcription factor. In response to taste-specific stimuli it induces cell-type-specific mRNA and protein expression. A week after the beginning of the experiment and two hours after the last feeding session, the mice are euthanized and their brains are preserved with a fixative such as 4% paraformaldehyde.

[4.] Identifying loci c-Fos expressing cells. The brains are sectioned and incubated with two types of antibodies. First, the brain sections are incubated with anti-c-Fos antibody. Next, they are incubated in an antibody raised against the c-Fos antibody. That second antibody is stained with fluorescence suitable for flow cytometry. Thus, the cells that expressed c-Fos in response to sweet-tasting liquid are stained with one type of fluorescence and the cell expressing c-Fos in response to MSG-specific taste are stained with a different fluorescence dye. The use of fluorescence microscope identifies the loci of the c-Fos expressing cells.

[5.] Using Cell Sorting to Partition Cells of Interest from Others.

[5.0] Flow cytometry. The ability to separate any cell type of interest from other cell types is essential for the identification of cell-type-specific proteins. Flow cytometry is one technique for sorting cells. In flow cytometry, cells are suspended in a stream of fluid, allowing simultaneous multiparametric analysis of the physical and/or chemical characteristics of single cells flowing through an optical and/or electronic detection apparatus. Fluorescence-activated cell-sorting (FACS™) is a specialized type of flow cytometry. It provides a method for sorting a heterogeneous mixture of biological cells into two or more containers, one cell at a time, based on the specific light scattering and fluorescence characteristics of each cell. The cell suspension is entrained in the center of a narrow, rapidly flowing stream of liquid. Just before the stream breaks into droplets, the flow passes through a fluorescence measuring station where the fluorescent character of interest for each cell is measured. An electrical charging ring is placed just at the point where the stream breaks into droplets. A charge is placed on the ring based on the immediately prior fluorescence intensity measurement and the opposite charge is trapped on the droplet as it breaks from the stream. The charged droplets then fall through an electrostatic deflection system that diverts droplets into containers based upon their charge. The stream is then returned to neutral after the droplet breaks off.

[5.1] Sample preparation for cell sorting. Adult mice are killed by cervical dislocation, and periventricular tissue is dissected into HEPES (4-(2-hydroxyethyl)-1-piperazineethanesulfonic acid)-buffered Eagle's medium (HEM). Then, the CNS tissue is diced then transferred to Mg2+/Ca2+-free HBSS (containing 10 mM HEPES at pH 7.6, 200 gml-1 EDTA, 0.5 mM trypsin, 0.001% DNase), for twenty minutes at 37 C. Six milliliters of HEM with 5% fetal calf serum (FCS) is added, and tissue is collected by centrifugation (7 minutes at 100 g). The supernatant is removed and the pellet triturated in 200 ml PBS (pH 7.4), producing a single-cell suspension that is subsequently passed through a 70-mm cell strainer, such as Falcon™, to remove debris.

[5.2] Immunostaining. The suspension is incubated with primary antibody (Santa Cruz Biotechnology) for the anti c-Fos antibodies then rinsed twice with PBS by centrifugation, and finally with phosphate buffer saline (PBS). For secondary antibody use either fluorescein isothiocyanate (FITC) or Phycoerythrin (PE) conjugate anti-rabbit antibody then rinsed twice with PBS by centrifugation. After these cell preparations were washed in sheath fluid, they are ready for the running on to cell sorter. Check sheath fluid tank and dispenser tank before using the cell sorter. Turn machine on ten minutes before use.

[5.3] Cell sorting. The cell sorting equipment is attached to computer system that is controlled by an application-specific software such as the Cell Quest™. Run the software first to calibrate with calibration kit. Then, to run a sample, turn the machine to RUN TEST mode. The green laser, FL1, is used with FITC conjugated antibodies, orange laser, FL2, is used with the PE conjugated antibodies. Wash the unit with sheath fluid after every sample run. C-Fos positive cells can be quantified using the graphs on the same run. The c-Fos positive cells were collected in one tube. Remove the cells and replace the tube.

[6.] Identifying differentially expressed cell-type-specific proteins. Differentially expressed cell-type-specific proteins can be identified by using two-dimensional gel electrophoresis (2-D GE). The technique described below, two-dimensional fluorescence difference gel electrophoresis (2-D DIGE) is an improvement over the conventional 2-D GE technique, involving fluorescent cyanine staining of proteins, which allows better quantification and comparison between different samples.

[6.1] Removing antibody from the cells. In the previous step, we have separated c-Fos-positive cell from the other cells using flow cytometry. Now, antibodies on c-Fos positive cells should be eluted by using glycine-HCl and EDTA (acid/EDTA). Heat at 56 degrees C., for ten minutes, or use the chloroquine method. Then, the cells will be ready for the protein extraction. As control, process c-Fos-negative cells in the same.

[6.2] Cell lysis and protein extraction. Cell should be lysed using appropriate isoelectric focusing lysis buffer, mainly containing a denaturing agent (urea), solubalizing agent (detergent-like triton X100) and protease inhibitor (cocktail) reductant dithiothreitol (DDT) at pH 8.5. In order to remove non-protein components, protein are precipitated using ammonium acetate in methanol, and then lipids should be removed using 80% acetone. Then, treat the cells with DNAse/RNAse. After removal of all other components, re-suspend the proteins the in lysis buffer. Make sure not to heat sample above 37 C. Measure protein concentrations using the detergent-compatible protein assay kit (Bio-Rad).

[6.3] Fluorescent dyes labeling. First, label protein samples using cyanine dye. The control is labeled with Cy2, while the treated cells are labeled with Cy3 or Cy5. The dye concentration should be 400 μmol of dye per 50 μg of protein at pH 8.5. After labeling both control and treated cell samples are mixed and lysine is added to prevent cross-reaction.

[6.4] Separation in the first dimension. Use an electrophoresis unit such as IPGPhore™ (Amersham Biosciences). For the first dimension run, add the sample mixture to an equal amount of sample buffer, detergent amino-sulfobetaine 14 (ASB14), denaturing agent urea, thiourea, dithiothreitol (DTT) and carrier ampholytes. The first dimension separation is based on the movement of electrically charged protein along a pH gradient under the influence of an applied electric current. This process is called isoelectric focusing. The pH gradient is maintained by immobilized pH gradient strips provide wide range of pH 3-10 and are 24 centimeter long. Next, place sample on the strip holder, and strip is overlaid atop it, making sure that no air bubbles are present. Voltage applied first for warming up and re-hydration 20 volt for 10 hours. Then, according to ramping protocol for isoelectric focusing, apply 500 volt for one hour, 1000 volt for one hour, 8000 volt for 8 hours. Internal cooling should be used to protect protein form overheating.

[6.5] Separation in the second dimension. Second dimension separation involves the use of SDS-PAGE (sodium dodecyl sulphate-polyacrylamide gel electrophoresis) which separate protein according to their molecular weight. Gel preparations can be used of different size 16×14 centimeter or 16×20 centimeter (Amersham Bioscience). Gels should be cast at least 9 hours before use. Next, IPG strips are incubated in equilibration buffer (30% glycerol, 8 M urea, 1% SDS, 0.5% DTT, 0.2 mg/ml bromophenol blue 100 mM tris pH 6.8) for 15 minutes then wash with running buffer (tris/glycine/SDS). Place strips on the acrylamide gel. Let the gel run for 20 hours at 2 W.

[6.6] Imaging and data analysis. Once sample has been separated in the gel they are scanned for Cy2, Cy3 and Cy5 fluorescence using appropriate scanner such as Typhoon 9400 imager (Amersham Bioscience), Cy2, Cy3 and Cy5 images can be scanned using 488, 532 and 633 nanometers, respectively. Photomultiplier tube voltage is adjusted according to spot saturation intensity. Image analysis is fully computerized provided with software such as Decyder™2-D software. Now compare spots of cells of experimental and control animals.

[6.7] Protein analysis. Once the protein of interest is established, the next step is the identification of that protein by sequencing using MALDI-TOF MS (matrix-assisted laser desorption ionization time-of-flight mass spectrometry) or nanospray ionization mass spectrometry. Data generated using mass spectroscopy is submitted to MASCOT™ search engine (Matrix Science Ltd.) which uses NCBI for the identifying the sequence of the identified protein.

[7.] Identifying differentially expressed cell-type-specific mRNA. An alternative to using two-dimensional gel electrophoresis is the use of DNA microarrays. The technique described below, uses the Affymetrix GeneChip™ Whole Transcript (WT) array, which is designed to generate amplified and biotinylated sense-strand DNA targets from the entire expressed genome without bias. This assay ad associated reagents have been optimized specifically for use with the GeneChip™, and the probes on the arrays have been selected to be distributed throughout the entire length of each transcript. This protocol involves the following five stages:
7.1 rRNA reduction and preparation of total RNA with diluted poly-A RNA controls
7.2 Total RNA target labeling protocol
7.3 Hybridization, array washing, and staining
7.4 Scanning.

[7.1] rRNA reduction and preparation of total RNA with diluted poly-A RNA controls. First, isolate total RNA from mouse brain. Cells isolated by cell sorting (approximately 5000) should be collected in microcentrifuge tubes and processed using the PicoPure™ RNA isolation kit (Arcturus, Mountain View, Calif.). Preparations of dilutions of Poly-A RNA controls involve 1) RiboMinus probe hybridization, 2) rRNA reduction, and 3) concentration.

[7.2] Total RNA target labeling protocol. This stage involves eight steps:
7.2.1 Preparation of rRNA-reduced total RNA/poly-A RNA controls
7.2.2 First-cycle, first-strand cDNA synthesis
7.2.3 First-cycle, second-strand cDNA synthesis
7.2.4 First-cycle, cRNA synthesis and cleanup
7.2.5 Second-cycle, first-strand cDNA synthesis
7.2.6 Hydrolysis of cRNA and cleanup of single-stranded DNA
7.2.7 Fragmentation of single-stranded DNA
7.2.8 Labeling of fragmented single-stranded DNA

[7.3] Hybridization array washing and staining. This stage involves the use of the hybridization, wash, and stain kit, which is supplied by the manufacturer of the microarray. Follow the instructions detailed in the "Setting up an experiment" section of the software User's Guide and enter the experiment information into the operating software. Then, wash, stain, and scan a probe array.

[7.4] Scanning. Prior to use, let the array warm to room temperature following 4° C. storage and warm the laser for at least 10 minutes. The operating software also controls the Scanner 3000 7G. The probe array is scanned after the wash protocols are complete.

[8.] Selective inactivation of cell-type-specific protein. The identification of a cell-type-specific protein is validated if its inactivation selectively eliminates the function of that cell type. The elimination of the function of that cell type, in turn selectively eliminates a corresponding behavioral response. Thus, the inactivation of cell-type-specific protein of gustatory brain cells that determine and can evoke the sensation of sweet taste would eliminate the otherwise typical behavioral response to sweet-tasting liquid, without eliminating responses to any other basic tastant. A cell-type-specific protein can be inactivated by gene silencing, selective disruption of the translation of the mRNA of that protein, or by antibodies raised against that protein if it is membrane bound.

[8.0] Using lentiviral vectors to transfect brain cells with RNA interference (RNAi). By way of example, the method described below utilizes replication deficient lentiviral vectors to transfect brain cells with RNAi that would selectively disrupt translation of the protein of interest. Lentiviral vectors can be constructed to deliver sense or antisense molecules with an infection efficiency of 100% in mouse models, and can be injected directly into the brain and infect virtually all cell types. The first step in the construction of the vector requires knowledge of the specific splice variant that needs to be targeted. The vector will target a unique exon/exon junction that has specific expression in the cells of interest. By designing an antisense RNA molecule that hybridizes on the mRNA across this unique junction, the process can produce a double-stranded RNA (dsRNA) molecule will be produced of sufficient size to activate the RNA interference pathway.

[8.1] Designing siRNA. The RNA interference (RNAi) pathway is activated by short interfering RNA (siRNA) molecules that are 21-23 nucleotides in length. After obtaining sequence data across the unique exon/exon junction, a 21-23-nucleotide sequence is synthesized corresponding to the antisense of roughly 11 bases on one exon and 12 bases on the other exon. Use BLAST check mouse genome database and insure that the conjunction of the 11 and 12 nucleotide sequences would not hybridize with any other coding regions. The synthesized oligonucleotide is then cloned into a U6 expression plasmid at the Xho1 and Nsi1 sites on the plasmid. This construct uses the U6 small nuclear RNA promoter to control transcription of the subcloned antisense sequence by RNA polymerase III, and can generate as many as five million short RNA molecules per cell after transfection.

[8.2] Three plasmid expression system construction. To construct the lentivirus, digest the U6 plasmid with BamH1 and EcoR1 and excise the U6 cassette. Ligate the construct into the SIN-PGK transfer vector and select clones that have the insert in the correct orientation. This vector also contains the gene for green fluorescent protein (GFP) and could be useful for down-stream analysis of infected cells. The infective virus can then be obtained by transient co-transfection of the transfer vector and envelope protein-coding plasmid, pMD.G, and packaging construct pCMVΔR8.91, into 293T cells.

[8.3] Transfection. Concentrated lentivirus expressing the antisense of interest can be injected into CD-1 nude mice intracranialy in a volume of 5 μl ($4 \times 10^8$ IU of vector)[2]. The RNAi pathway would be triggered only in cells expressing the splice variant of interest, disrupting the translation of its mRNA thus inactivating that cell type.

[8.4] Verification of knockdown. RNAi knockdown is verified first in vitro and then in vivo. The first step is to culture cells that express the unique splice variant and expose them to the lentivirus in vitro. This cell population can be isolated by cell sorting using the same c-Fos labeling technique that was used to identify the unique splice-variant of mRNA in the first place. As the RNA interference pathway targets mRNA, one way to analyze the effectiveness of the intended target knockdown is by quantitative realtime-PCR (qRT-PCR) to measure target transcript levels in gene-specific lentivirus-treated cells versus negative control lentivirus treated cells. TaqMan™ Gene Expression Assays from vendors such as Applied Biosystems have kits available for more than 41 thousand human and mouse genes and are suitable for this purpose. The first step in this process will be to determine what templates will be used, and which will be used in the dilution series. At least one template should have a dilution series of five 10-fold dilutions. For the primer set being used, the best annealing temperature can be determined by doing end-point PCR using a gradient for the annealing temperature. Choose the highest temperature with the best band. Utilize this temperature for the qRT-PCR reaction. Because of the temperature specificity of this technique, different primer sets must be done in separate runs, unless the best annealing temperature is the same for two sets. The qRT-PCR reaction and analysis can now be carried out according to the manufacture's instructions. After verifying the intended gene target knockdown in vitro, verify it in vivo. Optimally, the target gene has a corresponding antibody available and is membrane localized, so that protein levels can be monitored by standard fluorescence microscopy. Otherwise, whole mount in situ hybridization using a digoxigenin (DIG) labeled probe targeting the unique exon should be carried out. Fix transfected mouse brains in by an appropriate fixative such as 4% paraformaldyhide and dehydrate the samples in methanol.

[8.5] Imaging mRNA expression. Use in situ hybridization to visualize mRNA expression in tissues and cells of interest. A fluorophore-labeled mRNA probe that has consensus sequence to mRNA of interest is hybridized to the fixed tissues or cells. The resultant fluorescence will be detected when imaged with a fluorescent microscope. The overall procedure includes: 1) Synthesis (expression) of mRNA probe; 2) fluorescence labeling of the mRNA probe; 3) fixation and hybridization of the specimen, and 4) mounting of the specimen and microscopic imaging.

[8.6] Validation. A group of mice whose brain cells were transfected with RNAi antisense sequence against cell-type-specific protein of cells that determine and can evoke the sensation of sweet taste are fed by liquids with the different basic tastes. The identification of a protein is validated if its inactivation selectively eliminates the behavioral response to sweet tastants without eliminating responses to other tastants.

N. Using Human Brain Tissue Samples

[1] Localization. The spatial resolution of present-day non-invasive brain imaging techniques approaches that of a single cortical column. When medically required, deep brain stimulation (DBS) provides higher spatial resolution in response to selected stimuli.

[2.] Protein specificity. Tissue samples from human brain banks provide the basis for identifying mRNA and cell-type-specific proteins of locus-specific cells. Such identification is made possible by the effects of plasticity.

[3.] Pain. Basic forms of pain are innate unitary subjective states. The sensation of pain is determined and can be evoked by the intrinsic function of locus-specific cells. That intrinsic function, in turn, is determined by the protein specificities of those cells. The locus-specific cells that determine and can evoke the sensation of pain are depleted in comparison to normal brains in persons who have congenital insensitivity to pain. The contrast between brain tissue sample from a person who had normal pain response to those of a person who had congenital insensitivity to pain is a basis for identifying the cell-type-specific proteins of cells that determine and can evoke the sensation of pain.

[4.] Fear. Fear, like all basic emotions, is a unitary subjective state. Cells in the central nucleus of the amygdala determine and can evoke the sensation of fear. Person with bilateral damage to these central nuclei, such as the genetic disease Urbach-Wiethe have an impaired sensation of fear. Contrasts of brain tissue samples of the central nuclei between persons who had normal fear response to those who did not is a basis for identifying the cell-type-specific proteins of cells that determine and can evoke the sensation of fear.

[5.] Non-specific consciousness. Cells that determine and can evoke non-specific consciousness are associated with the non-specific thalamic nuclei. Contrasting tissue samples from non-specific thalamic nuclei of persons who died after being comatose for years with tissues from the same loci in a person who died of other causes may be the basis for identifying cell-type-specific proteins of cells that determine and can evoke non-specific consciousness.

CONCLUSIONS, RAMIFICATIONS AND SCOPE

[1.] Neural correlates of consciousness. The invention identifies the neural correlates of consciousness on the cellular level. It also conceptually identifies said correlates on the molecular level. This has never before been done. Two corollaries of said identification are:

[1.1] There exists a class of brain cells that Francis Crick called "awareness neurons."

[1.2] There exists a class of proteins that characterizes these brain cells.

[1.3] Identifying in other species the capacity to experience subjective states. The identification of the cell-type-specific proteins of brain cells that determine any unitary subjective state in humans would make it possible to identify their homologs in other species. This possibility, in turn, would allow the identification of the evolutionary stage at which a subjective state such as pain initially emerged. Some species have sensory capacities that are absent in humans. In these cases, it is possible to identify the cell-type-specific proteins of brain cells that determine the quality of said subjective states. This prospect makes it possible to produce transgenic animals with an enlarged variety or expanded range of unitary subjective states.

[2.] The genetic basis of dysfunction. The effects of the environment are mediated by the innate genetic mechanisms of the cell. Hence, all disease is, directly or indirectly, genetic. Genetic disease may be partitioned into region, tissue and tissue-specific cell type diseases and those that affect all cell types and are thus organism-wide (e.g. mitochondrial dysfunction). The following neural diseases exemplify cell-type and region-specific diseases.

| Disease | Brain region | Cell type |
| --- | --- | --- |
| Alzheimer disease | Hippocampus | Cholinergic neurons |
| Amyotrophic lateral sclerosis | Spine | Motor neurons |
| Huntington's disease | Striatum | GABAergic neurons |
| Multiple sclerosis | Central nervous system | Oligodendrocytes |
| Narcolepsy | Lateral hypothalamus | Hypocretin neurons |
| Parkinson disease | Substantia nigra | Dopamine neurons |

None of the present-day drugs for said diseases are cell-type-specific. Consequently, none of said diseases are curable by said drugs. Dysfunction that affects all cell types in an organism (e.g. housekeeping proteins) affects the entire organism, thus undermining the ability of the organism to effectively cope with cell-type-specific diseases. Mitochondrial dysfunction, for example, has an adverse effect on numerous specific diseases, including Alzheimer's disease and Parkinson's disease. For these reasons, the genome is the ultimate therapeutic target.

[3.] Some aspects of genetic disease. 1) Any gene in the genome is subject to mutation. 2) Most genetic mutations that can cause a serious or fatal disease are recessive. 3) Most persons are carriers of several recessive disease mutations. 4) Any said recessive genetic disease is expressed in persons who inherit it from both parents. 5) Numerous genetic disease mutations are haplotype-specific. For example, about 50% of recessive nonsyndromic of childhood deafness in Italian and Spanish populations is due to a mutation in the gap-junction protein connexin 26. In contrast, this mutation is rarely found in Asian populations. Sickle cell anemia is found mostly in Africans while Tay Sachs disease is found mostly in persons of (Ashkenazi) Jewish ancestry. 6) At present, genetic tests are used to identify newborns that are homozygous for a small number of serious or fatal diseases, such as severe combined immunodeficiency, cystic fibrosis or Tay Sachs disease. However, little can be done for those who test positive. This fact seems to have prompted ethicists to exclude tests for untreatable genetic diseases.

[4.] An Simple and Effective Way of Eliminating the Expression of Recessive Genetic Diseases.

[4.1] Testing newborns. Said untreatable genetic recessive diseases are preventable. The key is the institution of routine extensive genetic testing at birth. The plummeting cost of genetic testing now makes it possible to institute routine extensive genetic testing for newborns, including haplotype marker data. The results of such testing would form the most basic medical record of a person. Haplotype-related adverse drug reactions can be avoided if said information is available to physicians when prescribing medication. Persons who are recessive carriers of monogenic congenital deafness, for example, can avoid conceiving children who would be homozygous for that condition. Another example relates to significantly increased likelihood of Alzheimer's disease in persons homozygous to apolipoprotein epsilon4 (ApoE4/4). About 26% of the population is heterozygous for EpoE4. It is possible to avoid the conception of children who are ApoE4/4 if the information is available to the prospective parents. Here are the options available to persons who carry genes for serious or fatal genetic disease:

1) Knowingly bring into the world a child with a serious or fatal genetic disease
2) Have an amniocentesis test during the first trimester
3) Precede pregnancy with in vitro fertilization and pre-implantation diagnosis (PGD)
4) Avoid marriage or marry and avoid having children

[4.2] Pre-marital genetic tests. It will take time until persons who were tested after birth reach marrying age. In the interim period, that void can be filled by routine pre-marital genetic testing. It would be advisable to conduct routine pre-marital testing of mature couples. The replication-related error-correction in mitochondrial organelles is less efficient that in replication of nuclear DNA. As a result, mitochondria in mature persons contain numerous mutations, sharply increasing the frequency of pregnancies involving malformations, such as Down syndrome. Currently, in 90% of cases where an amniocentesis test identifies Down syndrome, couples choose not to continue the pregnancy to term. Pre-marital genetic testing could reduce the frequency of such abortions.

[4.3] Haplotype-specific drug testing, Haplotype diversity is one factor that underlies the differential response to drugs. The withdrawal from the market of recently introduced drugs (e.g. Vioxx, Celebrex, Tysabri and Crestor) has led to the suggestion of increasing of haplotype diversity of clinical drug test participants. It would be more effective to do the opposite: make drug tests haplotype-specific. The results would be less statistically variable. Haplotype-specific drug testing justifies a reduction in the required number of participants. This, in turn, would make it economically feasible to create such tests for several distinct haplotype groups.

[4.4] Prevention contrasted with somatic gene therapy or stem cell therapy. Stem cell therapy has the potential of curing, but not preventing genetic disease. Somatic gene therapy has been under development for diseases, such as severe combined immunodeficiency and cystic fibrosis. However, once routine genetic testing provides persons with information about being heterozygous carriers for a serious genetic disease, the need for stem cell therapy or somatic gene therapy for these diseases will decline sharply.

[4.5] Conclusion. The simplest and most effective way to improve general health is to recognize that ultimately, the genome is the therapeutic target. Consequently, in due course, extensive genetic testing at birth will be made routine. The results of these genetic tests would constitute the most basic part a person's medical record. Over the same period, clinical drug trials will be made haplotype-based. The institution of said routine genetic testing will make possible the virtual elimination of the expression of recessive genetic diseases.

What is claimed is:

1. A method of identifying protein specificities of locus specific brain cells that underlie unitary subjective states, including submodality-specific cortical loci of cell types that underlie submodality elements of exteroception-based sensation, comprising of the steps of:

establishing the three-level hierarchy of sensory modalities, submodalities and submodality elements whereby submodality elements do not contain any smaller constituents;

determining the class-inclusion membership of elements of a submodality and submodalities of a sensory modality;

establishing correspondence first between any said submodality element of sensation with external stimuli that elicits it, then between said element of sensation and a behavioral response, thus establishing correspondence between said stimuli and said behavioral responses, with the consequence that said response following said stimuli signifies the presence of said element of sensation and absence of said response following said stimuli signifies the absence of said element of sensation;

identifying cells in a submodality-specific area in a cerebral hemisphere that, following said stimuli, express immediate early genes, by using antibodies raised against specific expressed immediate early genes and segregating the early gene-expressing cells by using flow cytometry;

identifying cell-type-specific proteins in segregated cells using two-dimensional fluorescence difference gel electrophoresis;

eliminating the function of identified cell-type by inactivating the identified cell-type-specific protein using techniques including replication-deficient lentiviral vectors to transfect brain cells of model animal with RNA interference antisense sequence;

and validating identification of a particular protein by demonstrating that its inactivation selectively eliminates the function of said response of model animals to said stimuli without eliminating responses to stimuli that elicit other sensory elements within the same submodality.

* * * * *